(12) United States Patent
Andersen et al.

(10) Patent No.: US 8,623,331 B2
(45) Date of Patent: Jan. 7, 2014

(54) COMPRESSED CHEWING GUM TABLET

(75) Inventors: Carsten Andersen, Vejle (DK); Gitte Lorenzen, Vejle Øst (DK); Nicolai Arent, Horsens (DK); Bitten Thorengaard, Vejle Øst (DK); Helle Wittorff, Vejle Øst (DK)

(73) Assignee: Fertin Pharma A/S (DK)

( * ) Notice: Subject to any disclaimer, the term of this patent is extended or adjusted under 35 U.S.C. 154(b) by 0 days.

(21) Appl. No.: 12/819,932

(22) Filed: Jun. 21, 2010

(65) Prior Publication Data
US 2010/0255064 A1    Oct. 7, 2010

Related U.S. Application Data

(63) Continuation of application No. PCT/DK2007/000562, filed on Dec. 20, 2007.

(51) Int. Cl.
- *A61K 9/68* (2006.01)
- *A01N 43/40* (2006.01)
- *A61K 31/44* (2006.01)

(52) U.S. Cl.
USPC .............................................. 424/48; 514/343

(58) Field of Classification Search
USPC .............................................. 424/48; 514/343
See application file for complete search history.

(56) References Cited

U.S. PATENT DOCUMENTS

| | | |
|---|---|---|
| 5,227,154 A | 7/1993 | Reynolds |
| 5,300,305 A | 4/1994 | Stapler et al. |
| 5,378,131 A | 1/1995 | Greenberg |
| 5,580,590 A | 12/1996 | Hartman |
| 5,679,397 A | 10/1997 | Kuroda et al. |
| 5,800,848 A | 9/1998 | Yatka et al. |
| 5,866,179 A | 2/1999 | Testa |
| 6,013,287 A | 1/2000 | Bunczek et al. |
| 6,017,566 A | 1/2000 | Bunczek et al. |
| 6,194,008 B1 | 2/2001 | Li et al. |
| 6,235,318 B1 | 5/2001 | Lombardy, Jr. et al. |
| 6,344,222 B1 * | 2/2002 | Cherukuri et al. ............. 426/6 |

(Continued)

FOREIGN PATENT DOCUMENTS

| | | |
|---|---|---|
| CA | 2523510 A1 | 11/2004 |
| EP | 0711506 A2 | 5/1996 |

(Continued)

OTHER PUBLICATIONS

Food and Drug Administration, CFR, Title 21, Section 172,615, the Masticatory Substances, Synthetic; Apr. 1, 2005 edition; 2 pages.

(Continued)

*Primary Examiner* — Benjamin Packard
(74) *Attorney, Agent, or Firm* — St. Onge Steward Johnston & Reens LLC

(57) ABSTRACT

A compressed chewing gum tablet includes at least a first and a second chewing gum module, the first chewing gum module including a first chewing gum composition including at least a first active ingredient and chewing gum granules containing gum base, the second chewing gum module including a second chewing gum composition including at least a second active ingredient and chewing gum granules containing gum base, wherein the first active ingredient is a pharmaceutically active ingredient, and the second active ingredient is selected from the group consisting of pharmaceutically active ingredients and enhancers, wherein the gum base content of the first and second chewing gum modules is different.

10 Claims, 3 Drawing Sheets

(56) References Cited

U.S. PATENT DOCUMENTS

| | | |
|---|---|---|
| 6,436,899 B2 | 8/2002 | Portman |
| 6,468,962 B1 | 10/2002 | Portman |
| 6,471,945 B2 | 10/2002 | Luo et al. |
| 6,479,071 B2 | 11/2002 | Holme et al. |
| 6,485,739 B2 | 11/2002 | Luo et al. |
| 6,558,690 B2 | 5/2003 | Portman |
| 6,613,363 B1 | 9/2003 | Li |
| 6,685,916 B1 | 2/2004 | Holme et al. |
| 6,696,044 B2 | 2/2004 | Luo et al. |
| 6,716,815 B2 | 4/2004 | Portman |
| 6,733,818 B2 | 5/2004 | Luo et al. |
| 6,773,730 B1 | 8/2004 | Liu et al. |
| 6,838,431 B2 | 1/2005 | Portman |
| 6,846,500 B1 | 1/2005 | Luo et al. |
| 6,858,238 B2 | 2/2005 | Lee et al. |
| 2001/0021694 A1 | 9/2001 | Portman |
| 2001/0043907 A1 | 11/2001 | Luo et al. |
| 2002/0071858 A1 | 6/2002 | Luo et al. |
| 2002/0098157 A1 | 7/2002 | Holme et al. |
| 2002/0110580 A1 | 8/2002 | Portman |
| 2002/0119915 A1 | 8/2002 | Portman |
| 2002/0159955 A1 | 10/2002 | Luo et al. |
| 2003/0008810 A1 | 1/2003 | Portman |
| 2003/0099741 A1 | 5/2003 | Gubler |
| 2003/0124064 A1 | 7/2003 | Luo et al. |
| 2003/0157213 A1 | 8/2003 | Jenkins |
| 2003/0206993 A1 | 11/2003 | Gubler |
| 2003/0215417 A1 | 11/2003 | Uchiyama et al. |
| 2004/0001903 A1 | 1/2004 | Lee et al. |
| 2004/0081713 A1 | 4/2004 | Maxwell et al. |
| 2004/0115305 A1 | 6/2004 | Andersen et al. |
| 2004/0136928 A1 | 7/2004 | Holme et al. |
| 2005/0008732 A1 | 1/2005 | Gebreselassie et al. |
| 2005/0025721 A1 | 2/2005 | Holme et al. |
| 2006/0051455 A1* | 3/2006 | Andersen et al. .................. 426/3 |
| 2006/0147580 A1* | 7/2006 | Nissen et al. ...................... 426/3 |
| 2006/0198873 A1* | 9/2006 | Chan et al. ..................... 424/443 |
| 2007/0043200 A1 | 2/2007 | Yamamoto et al. |
| 2008/0181933 A1* | 7/2008 | Johnson et al. ................ 424/440 |
| 2010/0104688 A1* | 4/2010 | Andersen et al. .................. 426/5 |
| 2010/0104689 A1* | 4/2010 | Thorengaard ..................... 426/5 |

FOREIGN PATENT DOCUMENTS

| | | |
|---|---|---|
| EP | 1474993 A1 | 11/2004 |
| EP | 1554935 A1 | 7/2005 |
| EP | 1693086 A1 | 8/2006 |
| EP | 1545234 B1 | 7/2008 |
| WO | 0025598 A1 | 5/2000 |
| WO | 02102357 A1 | 12/2002 |
| WO | 2004004480 A1 | 1/2004 |
| WO | 2004028270 A1 | 4/2004 |
| WO | 2004032644 A2 | 4/2004 |
| WO | 2004098305 A1 | 11/2004 |
| WO | 2006000232 A1 | 1/2006 |
| WO | 2006002622 A1 | 1/2006 |
| WO | 2006079343 A1 | 8/2006 |
| WO | 2006127618 A2 | 11/2006 |

OTHER PUBLICATIONS

International Preliminary Report on Patentability and Written Opinion of the International Searching Authority; PCT/DK2007/000562; Jun. 22, 2010; 6 pages.

International Search Report; PCT/DK2007/000562; Sep. 12, 2008; 2 pages.

H.P. Fiedler, Lexikon der Hilfsstoffe für Pharmacie, Kosmetik and Angrenzende Gebiete, pp. 63-64 (1981).

* cited by examiner

COMPRESSED CHEWING GUM TABLET

CROSS-REFERENCE TO RELATED APPLICATIONS

The present application is a continuation of pending International patent application PCT/DK2007/000562 filed on Dec. 20, 2007 which designates the United States and the content of which is incorporated herein by reference.

The invention disclosed and claimed herein and the subject matter related thereto was developed pursuant to a joint research agreement between Fertin Pharma NS and Gumlink A/S, both of Denmark.

FIELD OF THE INVENTION

The present invention relates to the field of compressed chewing gum. In particular, the present invention provides improved possibilities of controlling the release of active ingredients from a compressed chewing gum tablet.

BACKGROUND OF THE INVENTION

A problem related to compressed chewing gum is that it may be difficult to obtain the same prolonged release of active ingredients as may be obtained in conventionally mixed chewing gum as compressed chewing gum tends to release active ingredients relatively fast.

A further problem related to conventional compressed chewing gum is that active ingredients may differ significantly in nature as the active ingredients may be contained in different delivery systems if such systems are applied. A further problem is that the desired release of the individual active ingredient may be difficult to control, thereby resulting in a non-synchronized release of different active ingredients which need to be synchronized.

It is therefore an object of the present invention to provide improved possibilities of designing a release profile according to a present desire.

SUMMARY OF THE INVENTION

The invention relates to a compressed chewing gum tablet comprising at least a first and a second chewing gum module,
  said first chewing gum module comprising a first chewing gum composition comprising at least a first active ingredient and chewing gum granules containing gum base,
  said second chewing gum module comprising a second chewing gum composition comprising at least a second active ingredient and chewing gum granules containing gum base,
  wherein said first active ingredient is a pharmaceutically active ingredient, and
  said second active ingredient is selected from the group consisting of pharmaceutically active ingredients and enhancers,
  wherein the gum base content of said first and second chewing gum modules is different.

The invention facilitates that different pharmaceutically active ingredients in different modules may be affected individually by the content of gum base contained in the different respective modules, thereby obtaining an improved administration of different pharmaceutically active ingredients with respect to a desired release and according to a desired synchronism. The desired synchronism may both involve that two different active ingredients are released at the same time and may also involve an offset.

In some embodiments it may be desired to have a fast release of a first active ingredient and a slower release of a second active ingredient.

The release may be controlled by the different gum base content of the modules, whereby a number of possibilities arise of designing a release profile of the active ingredients as desired.

In an embodiment of the invention, the first and second active ingredients are the same.

With the use of the same active ingredient as the first and second active ingredient and release controlling both of these it is e.g. possible to obtain a "quick shot" of the active ingredient upon initial chewing but also maintain a release of the same active ingredient over some time.

In an embodiment of the invention, the first and second active ingredients are different.

Using different active ingredients may e.g. be advantageous when the two ingredients are collaborating, e.g. the one active ingredient enhances the uptake of the other, or the first ensures an advantageous pH-level for the second active ingredient. However in some embodiments it may also be advantageous to have two or more independent active ingredients in the same chewing gum tablet.

In an embodiment of the invention, said first chewing gum composition comprises a further active ingredient different from said first active ingredient.

According to embodiments of the invention two or more active ingredients may be present in said first chewing gum composition. In this manner a number of combinations of active ingredients may be delivered from a single chewing gum tablet.

In an embodiment of the invention, wherein said second chewing gum composition comprises a further active ingredient different from said second active ingredient.

According to embodiments of the invention two or more active ingredients may be present in said second chewing gum composition. In this manner a number of combinations of active ingredients may be delivered from a single chewing gum tablet.

In an embodiment of the invention, wherein said active ingredients in said first chewing gum module are at least partly contained within said chewing gum granules.

In an embodiment of the invention, wherein said active ingredients in said second chewing gum module are at least partly contained within said chewing gum granules.

In an embodiment of the invention, the gum base content is different with respect to composition.

With a gum base content different with respect to composition, release profiles may be adjusted in that an active ingredient contained within a chewing gum granule will be released slower than an active ingredient which is added to the chewing gum layer outside the granules prior to compression. Hereby a desired amount of an active ingredient which is to be released relatively slowly may be added into the granules of the composition and another amount of the same or another active ingredient which is to be released relatively slowly may be added to the composition outside the granules, whereby a faster release of these are ensured.

In an embodiment of the invention, the gum base content is different with respect to weight.

With a gum base content different with respect to weight, release profiles may be adjusted in that e.g. an active ingredient in a module without any gum base may tend to release faster than an active ingredient in a module with a relatively large amount of gum base. Hence it seems that release profile control may be controlled by selecting a certain amount of gum base for each module.

In an embodiment of the invention, the gum base content is different with respect to the size of applied chewing gum granules.

With a gum base content different with respect to the size of applied chewing gum granules, release profiles may be adjusted in that indications have been seen that the release rate is different depending on an average size of the granules of the module, in which the active ingredient is positioned.

In an embodiment of the invention, wherein the size of the applied chewing gum granules is less in said first chewing gum module than in said second chewing gum module.

In an embodiment of the invention, the gum base content is different with respect to the degree of mixing with the active ingredient.

A further way to have different gum base content of two modules is to mix the two compositions with active ingredients differently, e.g. mixing the active ingredient more thoroughly into one composition than into the other.

In an embodiment of the invention, at least one of said first and second chewing gum composition facilitates a bi-phasic release of said second active ingredient.

In an embodiment of the invention, wherein said compressed chewing gum tablet comprises control means to at least partly synchronize the release of said at least one pharmaceutically active ingredient and the release of said at least one enhancer.

In an embodiment of the invention, said enhancer is a pH control agent.

In an embodiment of the invention, said pharmaceutically active ingredient is nicotine and/or varenicline.

In some embodiments nicotine is added as a salt such as nicotine bitartrate, nicotine pftalate, nicotine polacrilex, nicotine sulphate, nicotine tartrate, nicotine citrate, or nicotine lactate. Varenicline is often added as varenicline tartrate.

In an embodiment of the invention, the pharmaceutically active ingredients are selected from the group consisting of antihistamines, anti-smoking agents, agents used for diabetes, decongestants, peptides, pain-relieving agents, antacids, nausea-relieving agents, statines, or any combination thereof.

In an embodiment of the invention, the pharmaceutically active ingredients are selected from the group consisting of cetirizine, levo cetirizine, nicotine, nicotine polacrilex, nicotine in combination with alkaline agents, metformin, metformin HCL, phenylephrine, GLP-1, exenatide, MC-4 receptor antagonist, PPY(3-36), deca-peptide, KSL-W (acetate), fluor, chlorhexidine, or any combination thereof.

In an embodiment of the invention, the pharmaceutically active ingredients are selected from the group consisting of
loratadine, des-loratadine, nicotine bitartrate, nicotine in combination with caffeine, nicotine antagonists, combinations thereof or compounds comprising one or more of these, pseudoephedrine, flurbiprofen, paracetamol, acetylsalicylic acid, Ibuprofen, antacida, cimetidine, ranitidine, ondansetron, granisetron, metoclopramid, simvastatin, lovastatin, fluvastatin, acyclovir, benzydamin, rimonabant, varenicline, sildenafil, naltrexone, fluor in combination with fruit acids, derivatives, salts or isomers of chlorhexidine, or any combination thereof.

In an embodiment of the invention, said enhancers are selected from the group consisting of bile salts, cetomacrogols, chelating agents, citrates, cyclodextrins, detergents, enamine derivatives, fatty acids, labrasol, lecithins, phospholipids, synthetic and natural surfactants, nonionic surfactants, cell envelope disordering compounds, solvents, steroidal detergents, chelators, solubilization agents, charge modifying agents, pH control agents, degradative enzyme inhibitors, mucolytic or mucus clearing agents, membrane penetration-enhancing agents, modulatory agents of epithelial junction physiology, vasodilator agents, selective transport-enhancing agents, or any combination thereof. pH control agents include buffers.

In an embodiment of the invention, said enhancers are selected from the group consisting of cetylpyridinium chloride (CPC), benzalkonium chloride, sodium lauryl sulfate, polysorbate 80, Polysorbate 20, cetyltrimethylammonium bromide, laureth 9, sodium salicylate, sodium EDTA, EDTA, aprotinin, sodium taurocholate, saponins, bile salt derivatives, fatty acids, sucrose esters, azone emulsion, dextran sulphate, linoleic acid, labrafil, transcutol, urea, azone, nonionic surfactants, sulfoxides, sauric acid/PG, POE 23 lauryl ether, methoxysalicylate, dextran sulfate, methanol, ethanol, sodium cholate, Sodium taurocholate, Lysophosphatidyl choline, Alkylglycosides, polysorbates, Sorbitan esters, Poloxamer block copolymers, PEG-35 castor oil, PEG-40 hydrogenated castor oil, Caprocaproyl macrogol-8 glycerides, PEG-8 caprylic/capric, glycerides, Dioctyl sulfosuccinate, Polyethylene lauryl ether, Ethoxydiglycol, Propylene glycol, mono-di-caprylate, Glycerol monocaprylate, Glyceryl fatty acids ($C_8$-$C_{18}$) ethoxylated.

Oleic acid, Linoleic acid, Glyceryl caprylate/caprate, Glyceryl monooleate, Glyceryl monolaurate, Capryliccapric triglycerides, Ethoxylated nonylphenols, PEG-(8-50) stearates, Olive oil PEG-6, esters, Triolein PEG-6 esters, Lecithin, d-alpha tocopherol polyethylene glycol 1,000 succinate, Citric acid, Sodium citrate, BRIJ, Sodium laurate, 5-methoxysalicylic acid, Bile salts, Acetyl salicylate, ZOT, Docosahexaenoic acid, Alkylglycosides, Sodium glycocholate (GC-Na), Sodium taurocholate (TC-Na), EDTA, Choline salicylate, Sodium caprate (Cap-Na), N-lauryl-beta-D-maltopyranoside (LM), Diethyl maleate, Labrasol, Sodium salicylate, Mentol, Alkali metal alkyl sulphate, Sodium lauryl sulphate, Glycerin, Bile acid, Lecithin, phosphatidylcholine, phosphatidylserine, sphingomyelin, phosphatidylethanolamine, cephalin, lysolecithin, Hyaluronic acid: alkalimetal salts, sodium, alkaline earth and aluminum, Octylphenoxypolyethoxyethanol, Glycolic acid, Lactic acid, Chamomile extract, Cucumber extract, Borage oil (Hjulkrone olie), Evening primrose oil, Polyglycerin, Lysine, Polylysine, Triolein, Monoolein, Monooleates, Monolaurates, Polydocanol alkyl ethers, Chenodeoxycholate, Deoxycholate, Glycocholic acid, Taurocholic acid, Glycodeoxycholic acid, Taurodeoxycholic acid, Sodium glycocholate, Phosphatidylcholine, Phosphatidylserine, Sphingomyelin, Phosphatidylethanolamine, Cephalin, Lysolecithin, Alkali metal hyaluronates, Chitosan, Poly-L-arginine, Alkyl glucoside, Saccharide alkyl ester, Fusidic acid derivatives, Sodium taurdihydrofusidate (STDHF), L-α-phosphatidylcholine Didecanoyl (DDPC), Nitroglycerine, nitropruside, NOC5 [3-(2-hydroxy-1-(methyl-ethyl)-2-nitrosohydrazino)-1-propanamine], NOC12 [iV-ethyl-2-(l-ethyl-hydroxy-2-nitrosohydrazino)-ethanamine, SNAP [S-nitroso-N-acetyl-DL-penicillamine, NORI, NOR4, deacylmethyl sulfoxide, azone, salicylamide, glyceryl-l,3-diacetoacetate, 1,2-isopropylideneglycerine-3-acetoacetate), Amino acids, Amino acid salts, monoaminocarboxlic acids, Glycine, alanine, phenylalanine, proline, hydroxyproline, hydroxyamino acids, serine, acidic amino acids, aspartic acid, Glutamic acid, Basic amino acids, Lysine, N-acetylamino acids, N-acetylalanine, N-acetylphenylalanine, TM-acetylserine, N-acetylglycine, N-acetyllysine, N-acetylglutamic acid, N-acetylproline, N-acetylhydroxyproline, lactic acid, malic acid and citric acid and alkali metal salts thereof, pyrrolidonecarboxylic acids, alkylpyrrolidonecarboxylic acid esters, N-alkylpyrrolidones, proline acyl esters, sodium lauryl phosphate, sodium lauryl sulphate, sodium oleyl phosphate, sodium myristyl sulphate, polyoxyethylene alkyl ethers, polyoxyethylene alkyl esters, and caproic acid, alkylsaccharide, fusidic acid, polyethylene glycol, cetyl alcohol, polyvinylpyrolidone, Polyvinyl alcohol, Lanolin alcohol, Sorbitan monooleate, Ethylene glycol tetraacetic acid, Bile acid conjugate with taurine, Cholanic acid and salts, Cyclodextran, Cyclodextrin, Cyclodextrin (beta), Hydroxypropyl-β-cyclodextran, Sulfobutylether-β-cyclodextran, Methyl-β-cyclodextrin, Chitosan glutamate, Chitosan acetate, Chitosan hydrochloride, Chitosan hydrolactate, 1-O-alkyl-2-hydroxy-sn-glycero-3-phosphocholine, 3-O-alkyl-2-acetoyl-sn-glycero-1-phosphocholine, 1-O-alkyl-2-O-acetyl-sn-glycero-3-phospho(N,N,N-trimethyl)hexanolamine, Propylene glycol, Tetradecylmaltoside (TDM), Sucrose dedecanoate.

In an embodiment of the invention, said pH control agents are selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

In an embodiment of the invention, at least 50% of said chewing gum granules have an average diameter below 1600 µm.

In an embodiment of the invention, at least 50% of said chewing gum granules has an average diameter above 100 µm.

In an embodiment of the invention, said chewing gum granules substantially consists of gum base.

When a chewing gum granule as mentioned herein substantially consists of gum base, the result is gum base granules typically based mainly on natural and/or synthetic resins and/or elastomers. Such gum base granules may find application in combination with a variety of flavoring, sweetening and so on.

In an embodiment of the invention, said chewing gum granules comprise chewing gum ingredients.

In embodiments of the invention, the chewing gum granule may comprise chewing gum ingredients such as filler, coloring agent, flavoring agent, high-intensity sweetener, bulk sweetener, softener, emulsifier, acidulant, antioxidant, further conventional chewing gum ingredients and more.

In an embodiment of the invention, said chewing gum granules are agglomerates.

In an embodiment of the invention, said compressed chewing gum tablet comprises at least three individual coherent compressed modules.

In an embodiment of the invention, said active ingredient is selected from the group consisting of pharmaceuticals, nutraceuticals, medicaments, nutrients, nutritional supplements, drugs, dental care agents, herbals, and the like and combinations thereof.

In an embodiment of the invention, said active ingredient is selected from the ATC anatomical groups consisting of agents acting on:
A alimentary tract and metabolism, B blood and blood forming organs, C cardiovascular system, D dermatologicals, G genito urinary system and sex hormones, H systemic hormonal preparations, J antiinfectives for systemic use, L antineoplastic and immunomodulating agents, M musculo-skeletal system, N nervous system, P antiparasitic products, insecticides and repellents, R respiratory system and S sensory organs, V various, or any combination thereof.

In an embodiment of the invention, said active ingredient is selected from the ATC therapeutical groups consisting of:
A01 Stomatological preparations, A02 Drugs for acid related disorders, A04 Antiemetics and antinauseants, A06 Laxatives, A07 Antidiarrheals, intestinal anti-inflammatory/anti-infective agents, A08 Antiobesity preparations, excluding diet products, A10 Drugs used in diabetes, A11 Vitamins, A12 Mineral supplements, B01 Antithrombotic agents, B03 Antianemic preparations, C01 Cardiac therapy, C10 Serum lipid reducing agents, D01 Antifungals for dermatological use, G03 Sex hormones, G04 Urologicals, M01 Anti-inflammatory and antirheumatic products, M09 Other drugs for disorders of the musculo-skeletal system, N01 Anesthetics, N02 analgesics, N07 Other nervous system drugs, R01 Nasal preparations, R02 Throat preparations, R03 Drugs for obstructive airway diseases, R05 Cough and cold preparations, and R06 Antihistamines for systemic use, V01 allergens, V04 diagnostic agents, or any combination thereof.

In an embodiment of the invention, said active ingredient is selected from the therapeutical groups consisting of:
Antipyretic, Anti allergic, Anti-arrhythmic, Appetite suppressant, Anti-inflammatory, Broncho dilator, Cardiovascular drugs, Coronary dilator, Cerebral dilator, Peripheral vasodilator, Anti-infective, Psychotropic, Anti-manic, Stimulant, Decongestant, Gastro-intestinal sedative, Sexual dysfunction agent, Desinfectants, Antianginal substance, Vasodilator, Anti-hypertensive agent, Vasoconstrictor, Migraine treating agent, Anti-biotic, Tranquilizer, Anti-psychotic, Anti-tumor drug, Anticoagulant, Hypnotic, Sedative, Anti-emetic, Anti-nauseant, Anti-convulsant, Neuromuscular agent, Hyper and hypoglycaemic, Thyroid and anti-thyroid, Diuretic, Anti-spasmodic, Uterine relaxant, Anorectics, Spasmolytics, Anabolic agent, Erythropoietic agent, Anti-asthmatic, Expectorant, Cough suppressant, Mucolytic, Anti-uricemic agent, Dental vehicle, Breath freshener, Antacid, Anti-diuretic, Anti-flatulent, Betablocker, Teeth Whitener, Enzyme, Co-enzyme, Protein, Energy Booster, Fiber, Probiotics, Prebiotics, Antimicrobial agent, NSAID, Anti-tussives, Decongestrants, Anti-histamines, Anti-diarrheals, Hydrogen antagonists, Proton pump inhibitors, General nonselective CNS depressants, General nonselective CNS stimulants, Selectively CNS function modifying drugs, Antiparkinsonism, Narcotic-analgetics, Analgetic-antipyretics, Psychopharmacological drugs, diagnostica sex hormones allergens, antifungal agents, Chronic Obstructive Pulmonary Disease (COPD) or any combination thereof.

In an embodiment of the invention, said active ingredient is selected from the group consisting of: ace-inhibitors, antianginal drugs, antiarrhythrmas, anti-asthmatics, anti-cholesterolemics, analgesics, anesthetics, anticonvulsants, anti-depressants, anti-diabetic agents, anti-diarrhea preparations, antidotes, anti-histamines, anti-hypertensive drugs, anti-inflammatory agents, anti-lipid agents, antimanics, anti-nauseants, anti-stroke agents, anti-thyroid preparations, anti-tumor drugs, anti-viral agents, acne drugs, alkaloids, amino acid preparations, anti-tussives, antiuricemic drugs, anti-viral drugs, anabolic preparations, systemic and non-systemic antiinfective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, inmosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocryptine or nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

In an embodiment of the invention, said active ingredient is selected from the group consisting of anti-histamines, decongestants, smoking cessation aids, diabetes II agents, or any combination thereof.

In an embodiment of the invention, said active ingredient is selected from the group consisting of metformin, cetirizine, levo cetirizine, phenylephrine, flurbiprofen, nicotine, nicotine bitartrate, nicotine polacrilex, nicotine in combination with alkaline agents, nicotine in combination with caffeine, sodium picosulfate, fluor, fluor in combination with fruit acids, chlorhexidine, or any derivatives thereof, salts thereof, isomers thereof, nicotine antagonists, combinations thereof or compounds comprising one or more of these.

In an embodiment of the invention, said active ingredient is selected from the group consisting of ephedrine, pseudo ephedrine, caffeine, loratadine, sildenafil, simvastatin, sumatriptan, acetaminophen, calcium carbonate, vitamin D, ibuprofen, aspirin, alginic acid in combination with aluminum hydroxide and sodium bicarbonate, ondansetron, Tibolon, Rimonabant, Vareniclin, allergenes, sitagliptin or any derivatives thereof, salts thereof, isomers thereof, combinations thereof or compounds comprising one or more of these.

In an embodiment of the invention, said active ingredient is selected from the group consisting of phytochemicals, such as resveratrol and anthocyanine; herbals, such as green tea or thyme; antioxidants, such as polyphenols; micronutrients; mouth moisteners, such as acids; throat soothing ingredients; appetite suppressors; breath fresheners, such as zinc compounds or copper compounds; diet supplements; cold suppressors; cough suppressors; vitamins, such as vitamin A, vitamin C or vitamin E; minerals, such as chromium; metal ions; alkaline materials, such as carbonates; salts; herbals, dental care agents, such as remineralisation agents, antibacterial agents, anti-caries agents, plaque acid buffering agents, tooth whiteners, stain removers or desensitizing agents; and combinations thereof.

In an embodiment of the invention, said active ingredient is selected from the group consisting of di-peptides, tri-peptides, oligo-peptides, deca-peptides, deca-peptide KSL, deca-peptide KSL-W, amino acids, proteins, or any combination thereof.

In an embodiment of the invention, said active ingredient comprises a probiotic bacteria, such as lactobacilli, bifidobacteria, *lactococcus, streptococcus, leuconostoccus, pediococcus* or *enterococcus*.

In an embodiment of the invention, said active ingredient comprises a prebiotic, such as fructose, galactose, mannose, insulin or soy.

In an embodiment of the invention, said compressed chewing gum tablet comprises a center-fill.

In an embodiment of the invention, said center-fill is a liquid, a semi-liquid, or a solid composition.

In an embodiment of the invention, said center-fill is a solid or semi-liquid composition in combination with one or more enzymes suitable for enzymatic liquification of said solid or semi-liquid.

In an embodiment of the invention, said center-fill comprises bulk sweetener, high-intensity sweetener, flavor or combinations thereof.

In an embodiment of the invention, said compressed chewing gum tablet comprises one or more encapsulation delivery systems.

In an embodiment of the invention, said one or more encapsulation delivery systems comprise at least one encapsulating material and at least one ingredient encapsulated within said encapsulating material.

In an embodiment of the invention, at least one of said encapsulation material comprises PVA.

In an embodiment of the invention, at least one of said encapsulation material is selected from the group consisting of natural resin, such as a polyterpene resin; hydrogenated vegetable oil; wax; and combinations thereof.

In an embodiment of the invention, at least one of said encapsulation material comprises natural resin and PVA.

In an embodiment of the invention, at least one of said encapsulation material comprises an active ingredient.

In an embodiment of the invention, said chewing gum granules comprises biodegradable gum base.

In an embodiment of the invention, said biodegradable gum base comprises at least one biodegradable polyester polymer.

In an embodiment of the invention, said biodegradable gum base comprises at least one polymer selected from the group consisting of polyesters, poly(ester-carbonates), polycarbonates, polyester amides, polyhydroxy alkanoates, polypeptides, homopolymers of amino acids such as polylysine, proteins such as prolamin, and protein derivatives such as protein hydrolysates including a zein hydrolysate, or any combination thereof.

In an embodiment of the invention, said chewing gum granules are substantially free of non-biodegradable polymers.

In an embodiment of the invention, said compressed chewing gum is provided with an outer coating.

In an embodiment of the invention, said outer coating is selected from the group consisting of hard coating, soft coating and edible film-coating or any combination thereof.

In an embodiment of the invention, the chewing gum granules are formed through granulation and a following grinding.

When smaller granules are needed, the chewing gum granules may first be granulated and subsequently further grinded.

In an embodiment of the invention, the chewing gum granules have been granulated to an average particle size of below 1500 μm and further grinded to an average particle size of below 800 μm.

A grinding may preferably be carried out at a temperature of below 0° C., preferably below −10° C.

In an embodiment of the invention, said chewing gum composition comprises said gum base and one or more chewing gum ingredients.

In an embodiment of the invention, said chewing gum granules comprises said gum base and one or more chewing gum ingredients.

In an embodiment of the invention, at least a part of said one or more pharmaceutically active ingredients are mixed into said chewing gum mixture prior to granulation.

In an embodiment of the invention, said chewing gum granules comprise at least a part of said one or more pharmaceutically active ingredients.

In an embodiment of the invention, at least a part of the pharmaceutically ingredients are incorporated in at least a part of the chewing gum granules.

In an embodiment of the invention, at least a part of the pharmaceutically active ingredients are adhered to bulk sweetener particles by way of flavor.

In an embodiment of the invention, at least a part of the pharmaceutically active ingredients are adhered to chewing gum granules by way of flavor.

By the phrase "adhered to" it is implied that the association of two kinds of particles, e.g. pharmaceutically active ingredient particles and chewing gum granules or bulk sweetener in some cases is mediated by a third kind of particle, e.g. flavor particles.

In an embodiment of the invention, at least a part of the pharmaceutically active ingredients are adhered to dry binder particles.

The pharmaceutically active ingredients have average particle sizes which are relatively small, such as below 100 µm. It has been found advantageous to bind the pharmaceutically active ingredients to a dry binder and/or to the surrounding chewing gum granules and/or bulk sweetener particles. The free flowability of the pharmaceutically active ingredients in the chewing gum composition has thereby been reduced and thereby the tendency to segregation has been reduced. A relatively even distribution of pharmaceutically active ingredients in the chewing gum composition has been the result.

In an embodiment of the invention, said chewing gum granules comprise all of the one or more pharmaceutically active ingredients.

In an embodiment of the invention, said first and/or second chewing gum composition is having an evenly distributed desired concentration of said one or more pharmaceutically active ingredients.

In an embodiment of the invention, wherein the compressed chewing gum tablet comprises the pharmaceutically active ingredient in the form of metformin and the enhancers in the form of sodium glycolate and/or sodium laurylsulfate.

In an embodiment of the invention, wherein the compressed chewing gum tablet comprises the pharmaceutically active ingredient in the form of cetirizine and the enhancers in the form of polysorbate 80.

In an embodiment of the invention, wherein the compressed chewing gum tablet comprises the pharmaceutically active ingredient in the form of exenatide and the enhancers in the form of L-α-phosphatidylcholine Didecanoyl (DDPC).

In an embodiment of the invention, wherein the compressed chewing gum tablet comprises the pharmaceutically active ingredient in the form of nicotine polacrilex and the enhancers in the form of sodium carbonate.

In an embodiment of the invention, said gum base comprises two or more ingredients selected from the group consisting of elastomers, elastomer plasticizers, resins, polyvinyl acetate, hydrogenated resins, polyterpene resins, fillers, hydrogenated starch hydrolysate, fats and waxes, or any combination thereof.

In an embodiment of the invention, said chewing gum ingredients are selected from the group consisting of bulk sweeteners, flavors, dry binders, tabletting aids, anti-caking agents, emulsifiers, antioxidants, high intensity sweeteners, colors, or any combination thereof.

In an embodiment of the invention, the chewing gum granules comprise one or more chewing gum ingredients selected from the group consisting of bulk sweeteners, flavors, dry binders, tabletting aids, anti-caking agents, emulsifiers, antioxidants, or any combination thereof.

In an embodiment of the invention, one or more bulk sweeteners are provided as particles having average diameters below 700 µm, preferably below 500 µm.

In an embodiment of the invention, the particles of bulk sweetener have particle sizes in the range of 150 to 400 µm.

In an embodiment of the invention, the chewing gum granules have average diameters below 1500 µm, preferably below 1000 µm, more preferably below 800 µm, and most preferably below 600 µm.

In an embodiment of the invention, the average particle size of the chewing gum granules is at most 5 times larger, preferably at most 3 times larger, and most preferably at most 2 times larger than the average particle size of the bulk sweetener particles.

In an embodiment of the invention, the chewing gum granules and the bulk sweetener particles have average particle sizes deviating at most 600%, preferably at most 400% from each other.

In an advantageous embodiment of the invention, there are applied gum base granules and bulk sweetener particles having comparable particle sizes.

According to embodiments of the invention, powder segregation is reduced and a more even distribution of pharmaceutically active ingredients in the chewing gum composition is obtained by applying gum base granules and bulk sweetener particles having comparable particle sizes. Small particles of the pharmaceutically active ingredients are advantageously adhered to the larger particles by way of flavoring material or by way of a dry binder.

In an embodiment of the invention, the chewing gum composition is prepared by spraying one or more flavor materials onto the particles of bulk sweetener and letting particles of the pharmaceutically active ingredients adhere thereto.

In an embodiment of the invention, the chewing gum composition is prepared by spraying one or more flavor materials onto chewing gum granules and the particles of bulk sweetener and letting particles of the pharmaceutically active ingredients adhere thereto.

In an embodiment of the invention, an amount of dry binder is used to adhere API to bulk sweetener.

In an embodiment of the invention, the dry binders are selected from the group consisting of mikro-crystalline cellulose (MCC), silicified micro-crystalline cellulose (SMCC), spray dried lactose, fast flow lactose, anhydrous lactose, sucrose, mannitol, mannitol EZ, dextrose, fructose, sorbitol, povidone, copovidone, dicalcium phosphate (DCP), starch (corn, potato and rice), pre-gelatinized starch, or any combination thereof.

In an embodiment of the invention, the used amount of dry binder is in the range of 2% to 40%, preferably in the range of 3% to 30%, and most preferably in the range of 5% to 20% by weight of the chewing gum composition in at least one of the modules of the compressed chewing gum tablet.

BRIEF DESCRIPTION OF THE DRAWINGS

The invention will now be described with reference to the drawings of which

DETAILED DESCRIPTION OF THE INVENTION

In the prior art active ingredients may differ significantly in nature as the active ingredients may be contained in different delivery systems if such systems are applied and the release of the individual active ingredient may be difficult to control, thereby resulting in a non-synchronized release of different active ingredients which need to be synchronized. With the present invention, as described in the following, advantageous control of the release of the active ingredients is made possible.

AI (AI: Active ingredients) as used herein is used to cover e.g. API (API: pharmaceutically active ingredients) and enhancers.

The word granule throughout this document should be understood as broadly as possibly being powder, particles, agglomerates or the like. Generally the four terms may be used interchangeably.

The term "average diameter" as used herein is defined as the diameter of a sphere having the same volume as the granule or particle, which is the consequence of that granules may possess almost any shape, and according to the definition granules having the same volume also have the same average diameter.

Figures 1A, 1B:
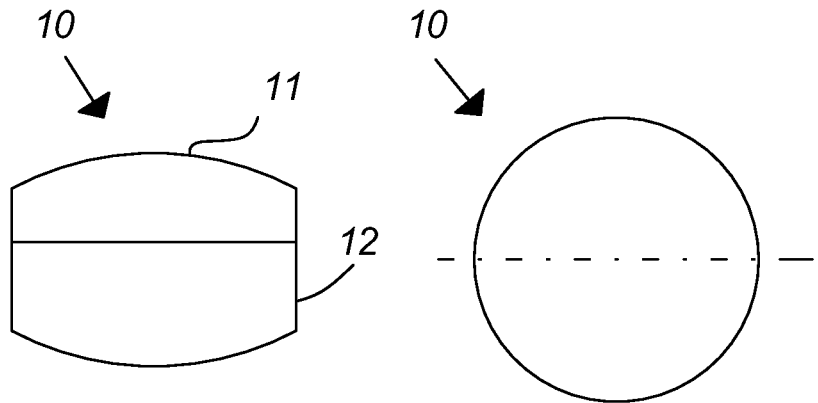
FIGS. 1a-1b illustrate a two-layer compressed tablet according to an embodiment of the invention.

FIG. 1a illustrates a cross-section of a compressed multi modular chewing gum tablet according the invention and illustrated in FIG. 1b.

The illustrated chewing gum tablet 10 comprises two chewing gum modules 11 and 12.

According to the illustrated embodiment, each module is simply comprised by a layer. The multi-module tablet may in this embodiment be regarded as a two-layer chewing gum tablet 10.

The illustrated chewing gum tablet 10 may for example weigh approximately 1.3 gram and comprise a first GB-containing chewing gum module 11 and a second GB-containing module 12 (GB: gum base).

The illustrated tablet has an approximate diameter of 16 mm and a thickness at the thickest point in the center of approximately 7 mm.

The two modules 11 and 12 are adhered to each other. Different processes may be applied for the purpose. However, according to a preferred embodiment of the invention, the mutual adhering between the two layers is obtained by the compression of one module 11 onto the other 12.

According to an embodiment of the invention, the illustrated chewing gum tablet 10 may be provided with a coating, e.g. a film coating.

It should be noted that various concentrations of gum base in the different modules (here: layers) may be applied within the scope of the invention.

The modules may for instance comprise compressible chewing gum ingredients, for example sweeteners and flavors, more or less pre-processed for the purpose of facilitating a true compression. Other optional ingredients to be emphasized here may e.g. comprise pharmaceutically active ingredients.

In other applications, e.g. for the purpose of establishing different release profiles the different modules may comprise different content of gum base.

The tablet may moreover comprise (not shown) one or several barrier layers adapted for establishment of a barrier between inter-reacting ingredients, such as certain acids and flavors.

Figures 2A, 2B:
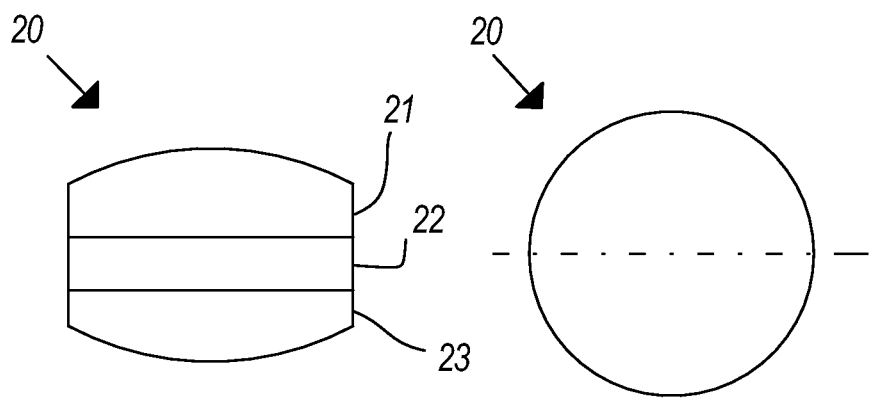
FIGS. 2a-2b illustrate a three layer compressed tablet according to an embodiment of the invention.

FIG. 2a illustrates a cross-section of a compressed multi modular chewing gum tablet according to an embodiment of the invention and illustrated in FIG. 2b from above.

The illustrated embodiment 20 comprises a three-module chewing gum of which the each of the layers 21, 22, and 23 optionally comprise a gum base incorporated chewing gum module having a certain gum base concentration. As an example layers 21 and 22 may contain gum base and layer 23 may be a substantially gum base-free chewing gum module.

A layer without gum base, which could be chewing gum module 23, may for example comprise compressed chewing gum ingredients, such as sweeteners, flavor, freeze-dried fruit, etc.

Modules containing gum base, here the two modules 21 and 22, may advantageously comprise different gum base content for the purpose of providing a desired release profile, whereas a non-GB module, here module 23, may ensure a fast release of an active ingredient or simply add an amount of bulk sweetener or other chewing gum ingredients, which are quickly released when the tablet is chewed.

Figures 2C, 2D:
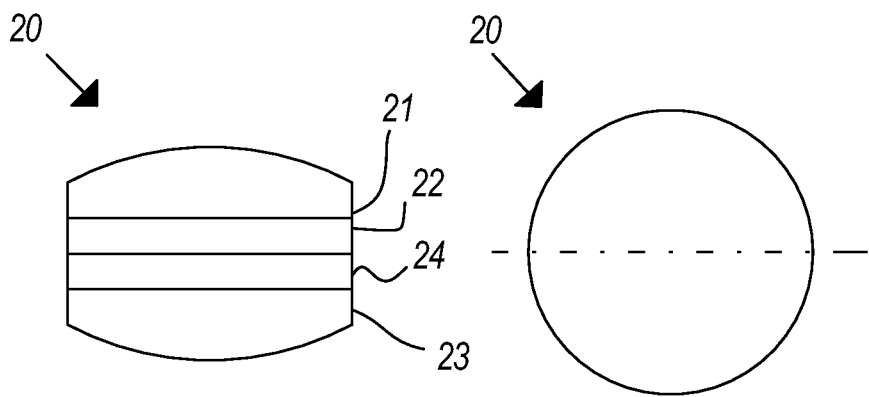
FIGS. 2c-2d illustrate a four layer compressed tablet according to an embodiment of the invention.

FIGS. 2c and 2d illustrate a cross-section of a compressed multi modular chewing gum tablet according to an embodiment of the invention with the same possibilities as explained above with reference to FIGS. 2a and 2b.

Figure 3A:
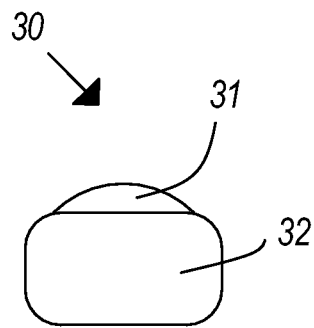
FIGS. 3a-3b illustrate a further two layer compressed tablet according to an embodiment of the invention.
Figure 3B:
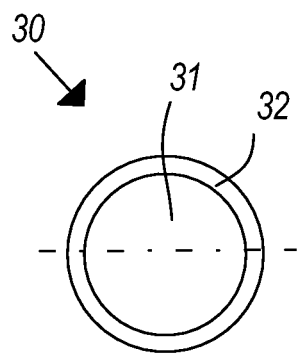

FIG. 3a illustrates a cross-section of a compressed multi modular chewing gum tablet 30 according the invention and illustrated in FIG. 3b from above.

The illustrated chewing gum tablet 30 comprises a gum base incorporated chewing gum module 32 upon which another gum base incorporated chewing gum base is arranged.

Figure 4A:
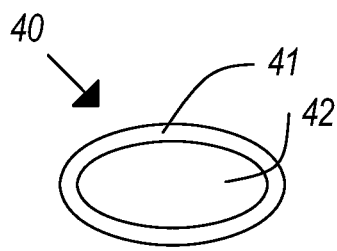
FIGS. 4a-4b illustrate a further two layer compressed tablet according to an embodiment of the invention.
Figure 4B:
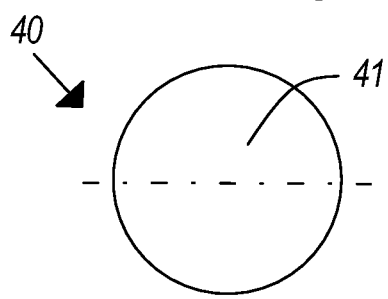

FIG. 4a illustrates a cross-section of a further compressed multi-modular chewing gum tablet 40 according to an embodiment of the invention and illustrated in FIG. 4b from above.

The tablet 40 differs somewhat from the other described tablets in the sense that the tablet comprises a compressed GB-incorporated chewing gum module 42 forming a gum center. The module 42 is encapsulated by a surrounding module 41.

Figure 5A:
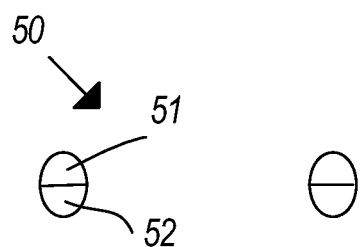
FIGS. 5a-5b illustrate a further two layer compressed tablet according to an embodiment of the invention, and where
Figure 5B:
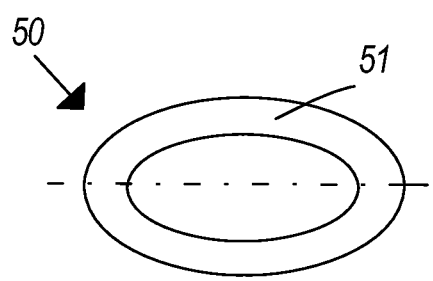

FIG. 5a illustrates a cross-section of a compressed multi-modular chewing gum tablet 50 according to an embodiment of the invention and illustrated in FIG. 5b from above.

According to the illustrated embodiment, showing a ring-formed two layer tablet 50, a base chewing gum module 52 comprises a certain concentration of gum base, whereas the other layer comprises another content of gum base 51.

Figure 6A:
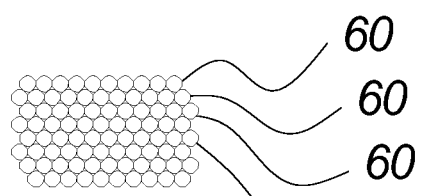
FIGS. 6a-6d illustrate cross-sectional views of different compositions usable according to some embodiments of the invention.
Figure 6B:
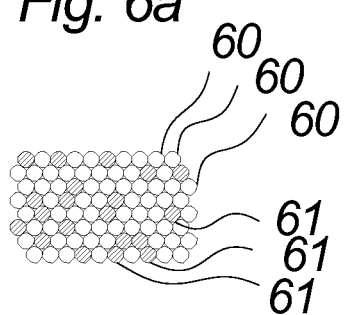
Figure 6C:
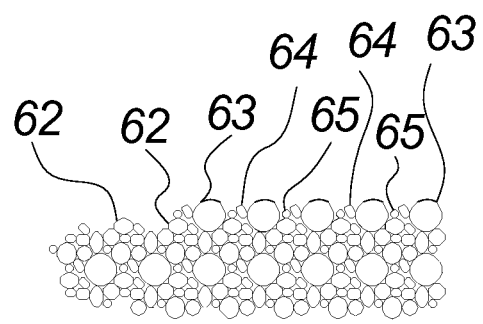

FIGS. 6a-6c illustrate compositions of granules according to embodiments of the invention, ready for being compressed to a module in a chewing gum tablet according to embodiments of the invention. In FIG. 6a the composition consists of granules 60 uniformly shaped and sized. FIG. 6c illustrates a composition of granules 62, 63, 64, 65 with varying shapes and sizes.

A composition of a mixture of chewing gum granules and bulk sweetener with flavor-"glued" AI may e.g. look as FIG. 6c, in which e.g. 62 and 63 could be chewing gum granules and e.g. 64 and 65 could be agglomerated bulk sweetener with flavor-"glued" AI.

Further a composition may look as in FIG. 6c wherein e.g. 63 is chewing gum granules with or without AI and 62, 64, 65 may be other typical chewing gum ingredients such as bulk sweetener, flavor, filler, etc.

Figure 6D:
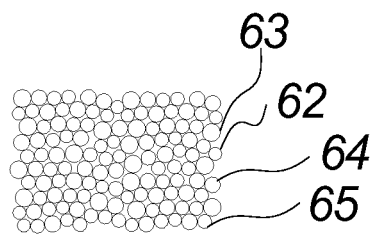

FIG. 6d illustrates a composition like in FIG. 6c, wherein an improved size distribution has been obtained in order to avoid segregation. With too large differences in the granule sizes segregation may be a problem, in that the smaller particles will tend to move more easily in a composition than the larger particles and hence a concentration of e.g. an active ingredient in a composition may be in a risk of being very different in a sample taken from the composition.

FIG. 6b illustrates a composition comprising a mixture of chewing gum granules 60 and agglomerated bulk sweetener with flavor-"glued" API 61, wherein the size of the chewing gum granules 60 and the agglomerated bulk sweetener with flavor-"glued" API 61 is essentially the same.

FIGS. 6a-6c are illustrative examples only of how compositions may look according to embodiments of the invention. As should be apparent from the content of the description, the compositions as mentioned herein may comprise active ingredients and gum base in different layers, wherein the AIs may be incorporated in the granules or added to the composition outside the granules as long as the gum base content is different and a desired release profile may be achieved.

The formulations, applied pharmaceutically active ingredients, examples of compositions and layers given herein are exemplary and only given for the purpose of evaluating and explaining different features of the invention. Compositions and the combinations of layers may be varied significantly within the scope of the invention. Specific variations and details with respect to ingredients, formulations and compositions within the scope of the invention are given below.

In accordance with the general principles in manufacturing a chewing gum tablet within the scope of the invention, variations of different suitable ingredients are listed and explained below.

Chewing gum of the present invention typically comprises a water-soluble portion, a water-insoluble chewable gum base portion and flavoring agents. The water-soluble portion dissipates with a portion of the flavoring agent over a period of time during chewing. The gum base portion is retained in the mouth throughout the chew. The term chewing gum refers to both a chewing and bubble type gum in its general sense.

The gum base is the masticatory substance of the chewing gum, which imparts the chew characteristics to the final product. The gum base typically defines the release profile of flavors and sweeteners and plays a significant role in the gum product.

The insoluble portion of the gum typically may contain any combination of elastomers, vinyl polymers, elastomer plasticizers, waxes, softeners, fillers and other optional ingredients such as colorants and antioxidants.

The composition of gum base formulations can vary substantially depending on the particular product to be prepared and on the desired masticatory and other sensory characteristics of the final product. However, typical ranges (% by weight) of the above gum base components are: 5 to 80% by weight elastomeric compounds, 5 to 80% by weight elastomer plasticizers, 0 to 40% by weight of waxes, 5 to 35% by weight softener, 0 to 50% by weight filler, and 0 to 5% by weight of miscellaneous ingredients such as antioxidants, colourants, etc. The gum base may comprise about 5 to about 95 percent, by weight, of the chewing gum, more commonly the gum base comprises 10 to about 60 percent, by weight, of the gum.

Elastomers provide the rubbery, cohesive nature to the gum, which varies depending on this ingredient's chemical structure and how it may be compounded with other ingredients. Elastomers suitable for use in the gum base and gum of the present invention may include natural or synthetic types.

Elastomer plasticizers vary the firmness of the gum base. Their specificity on elastomer inter-molecular chain breaking (plasticizing) along with their varying softening points cause varying degrees of finished gum firmness and compatibility when used in base. This may be important when one wants to provide more elastomeric chain exposure to the alkane chains of the waxes.

The elastomer compounds may be of natural origin but are preferably of synthetic origin, preferably synthetic polyesters.

It is noted that gum base or gum granules may also include components typically referred to as chewing gum ingredients.

The chewing gum may, according to embodiments of the invention, comprise conventionally non-biodegradable polymers, such as natural resins, synthetic resins and/or synthetic or natural elastomers.

According to an embodiment of the invention, at least a part of the polymers of the chewing gum are biodegradable.

In an embodiment of the invention, the chewing gum may comprise combinations of biodegradable polymers and polymers generally regarded as non-biodegradable, such as natural resins, synthetic resins and/or synthetic/natural elastomers.

In an embodiment of the invention, said natural resin comprises terpene resins, e.g. derived from alpha-pinene, beta-pinene, and/or d-limonene, natural terpene resins, glycerol esters of gum rosins, tall oil rosins, wood rosins or other derivatives thereof such as glycerol esters of partially hydrogenated rosins, glycerol esters of polymerized rosins, glycerol esters of partially dimerised rosins, pentaerythritol esters of partially hydrogenated rosins, methyl esters of rosins, partially hydrogenated methyl esters of rosins or pentaerythritol esters of rosins and combinations thereof.

Materials to be used for encapsulation methods may e.g. include Gelatine, Wheat protein, Soya protein, Sodium caseinate, Caseine, Gum arabic, Mod. starch, Hydrolyzed starches (maltodextrines), Alginates, Pectin, Carregeenan, Xanthan gum, Locus bean gum, Chitosan, Bees wax, Candelilla wax, Carnauba wax, Hydrogenated vegetable oils, Zein and/or Sucrose.

Examples of generally non-biodegradable synthetic resins include polyvinyl acetate, vinyl acetate-vinyl laurate copolymers and mixtures thereof. Examples of non-biodegradable synthetic elastomers include, but are not limited to, synthetic elastomers listed in Food and Drug Administration, CFR, Title 21, Section 172,615, the Masticatory Substances, Synthetic) such as polyisobutylene. e.g. having a gel permeation chromatography (GPC) average molecular weight in the range of about 10,000 to 1,000,000 including the range of 50,000 to 80,000, isobutylene-isoprene copolymer (butyl elastomer), styrene-butadiene copolymers e.g. having styrene-butadiene ratios of about 1:3 to 3:1, polyvinyl acetate (PVA), e.g. having a GPC average molecular weight in the range of 2,000 to 90,000 such as the range of 3,000 to 80,000 including the range of 30,000 to 50,000, where the higher molecular weight polyvinyl acetates are typically used in bubble gum base, polyisoprene, polyethylene, vinyl acetate-vinyl laurate copolymer e.g. having a vinyl laurate content of about 5 to 50% by weight such as 10 to 45% by weight of the copolymer, and combinations hereof.

The elastomers (rubbers) employed in the gum base may vary depending upon various factors such as the type of gum base desired, the texture of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle gum, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

It is common in the industry to combine in a gum base a synthetic elastomer having a high molecular weight and a synthetic elastomer having a low molecular weight. Examples of such combinations are polyisobutylene and styrene-butadiene, polyisobutylene and polyisoprene, polyisobutylene and isobutylene-isoprene copolymer (butyl rubber) and a combination of polyisobutylene, styrene-butadiene copolymer and isobutylene isoprene copolymer, and all of the above individual synthetic polymers in admixture with polyvinyl acetate, vinyl acetate-vinyl laurate copolymers, respectively and mixtures thereof.

Examples of natural resins are: Natural rosin esters, often referred to as ester gums including as examples glycerol esters of partially hydrogenated rosins, glycerol esters of polymerised rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

Chewing gums according to embodiments of the invention may be provided with an outer coating.

The applicable hard coating may be selected from the group comprising of sugar coating and a sugarless coating and a combination thereof. The hard coating may e.g. comprise 50 to 100% by weight of a polyol selected from the group consisting of sorbitol, maltitol, mannitol, xylitol, erythritol, lactitol and Isomalt and variations thereof. In an embodiment of the invention, the outer coating is an edible film comprising at least one component selected from the group consisting of an edible film-forming agent and a wax. The film-forming agent may e.g. be selected from the group comprising cellulose derivative, a modified starch, a dextrin, gelatine, shellac, gum arabic, zein, a vegetable gum, a synthetic polymer and any combination thereof. In an embodiment of the invention, the outer coating comprises at least one additive component selected from the group comprising of a binding agent, a moisture-absorbing component, a film-forming agent, a dispersing agent, an antisticking component, a bulking agent, a flavoring agent, a coloring agent, a pharmaceutically or cosmetically active component, a lipid component, a wax component, a sugar, an acid and an agent capable of accelerating the after-chewing degradation of the degradable polymer.

Generally, the ingredients may be mixed by first melting the gum base and adding it to the running mixer. Colors, active agents and/or emulsifiers may also be added at this time. A softener such as glycerin may also be added at this time, along with syrup and a portion of the bulking agent/sweetener. Further portions of the bulking agent/sweetener may then be added to the mixer. A flavoring agent is typically added with the final portion of the bulking agent/sweetener. A high-intensity sweetener is preferably added after the final portion of bulking agent and flavor has been added.

The entire mixing procedure typically takes from five to fifteen minutes, but longer mixing times may sometimes be required. Those skilled in the art will recognize that many variations of the above-described procedure may be followed. Including the one-step method described in US patent application 2004/0115305 hereby incorporated as reference. Chewing gums are formed by extrusion, compression, rolling and may be centre filled with liquids and/or solids in any form.

When manufacturing a compressed chewing gum tablet another method is applied, which is basically very different than the above described, but may broadly be described as an initial conventional mixing of the gum base, as above described, followed by a granulation of the obtained gum base mix. The obtained chewing gum granules may then be mixed with further chewing gum ingredients, such as sweeteners and flavor. This final granule mix may then be compressed under high pressure (typically when applying cooling) into a chewing gum tablet. For each compression a layer is made and in this way it is possible to make multi-layered chewing gums, such as two, three or four layers, wherein each layer may include an individual composition, i.e. different active ingredients may be used for medical purposes or different colors may be used for visual purposes, etc.

This type of chewing gum has been widely used especially within a segment of medical chewing gum due to the thereto-related relatively careful way of handling the chewing gum ingredients and especially the active ingredient typically being quite vulnerable to for example high temperatures.

In further embodiments of the present invention, a chewing gum may also be provided with an outer coating, which may be a hard coating, a soft coating, a film coating, or a coating of any type that is known in the art, or a combination of such coatings. The coating may typically constitute 0.1 to 75% by weight of a coated chewing gum piece.

One preferred outer coating type is a hard coating, which term is including sugar coatings and sugar-free (or sugarless) coatings and combinations thereof. The object of hard coating is to obtain a sweet, crunchy layer, which is appreciated by the consumer and to protect the gum centers. In a typical process of providing the chewing gum centers with a protective sugar coating the gum centers are successively treated in suitable coating equipment with aqueous solutions of crystallizable sugar such as sucrose or dextrose, which, depending on the stage of coating reached, may contain other functional ingredients, e.g. fillers, colors, etc.

In one presently preferred embodiment, the coating agent applied in a hard coating process is a sugarless coating agent, e.g. a polyol including as examples sorbitol, maltitol, mannitol, xylitol, erythritol, lactitol and isomalt or e.g. a mono-disaccharide including as example trehalose.

Or alternatively a sugar-free soft coating e.g. comprising alternately applying to the centers a syrup of a polyol or a mono-di-saccharide, including as examples sorbitol, maltitol, mannitol, xylitol, erythritol, lactitol, isomalt and trehalose.

In further useful embodiments, a film coating is provided by film-forming agents such as a cellulose derivative, a modified starch, a dextrin, gelatine, zein, shellec, gum arabic, a vegetable gum, a synthetic polymer, etc. or a combination thereof.

In an embodiment of the invention, the outer coating comprises at least one additive component selected from the group comprising a binding agent, a moisture-absorbing component, a film-forming agent, a dispersing agent, an antisticking component, a bulking agent, a flavoring agent, a coloring agent, a pharmaceutically or cosmetically active component, a lipid component, a wax component, a sugar, and an acid.

A coated chewing gum center according to embodiments of the invention may have any form, shape or dimension that permits the chewing gum center to be coated using any conventional coating process.

It should however be noted that application of different coating should be done with care as compressed chewing gum tablets may be negatively affected by direct contact with moisture or water.

The composition of gum base formulations can vary substantially depending on the particular product to be prepared and on the desired masticatory and other sensory characteristics of the final product. However, typical ranges of the above gum base components are: 5 to 80% by weight of elastomeric compounds, 5 to 80% by weight of elastomer plasticizers, 0 to 40% by weight of waxes, 5 to 35% by weight of softener, 0 to 50% by weight of filler, and 0 to 5% by weight of miscellaneous ingredients such as antioxidants, colorants, etc. The gum base may comprise about 5 to about 95% by weight of the chewing gum, more commonly; the gum base comprises 10 to about 60% by weight of the gum.

Elastomers provide the rubbery, cohesive nature to the gum, which varies depending on this ingredient's chemical structure and how it may be compounded with other ingredients. Elastomers suitable for use in the gum base and gum of the present invention may include natural or synthetic types.

Elastomer plasticizers vary the firmness of the gum base. Their specificity on elastomer inter-molecular chain breaking (plasticizing) along with their varying softening points cause varying degrees of finished gum firmness and compatibility when used in gum base. This may be important when one wants to provide more elastomeric chain exposure to the alkanic chains of the waxes.

If desired, conventional elastomers or resins may be supplemented or substituted by biodegradable polymers.

Biodegradable polymers that may be used in the chewing gum of the present invention may be homopolymers, copolymers or terpolymers, including graft- and block-polymers.

Useful biodegradable polymers, which may be applied as gum base polymers in the chewing gum of the present invention, may generally be prepared by step-growth polymerization of di-, tri- or higher-functional alcohols or esters thereof with di-, tri- or higher-functional aliphatic or aromatic carboxylic acids or esters thereof. Likewise, also hydroxy acids or anhydrides and halides of polyfunctional carboxylic acids may be used as monomers. The polymerization may involve direct polyesterification or transesterification and may be catalyzed.

The usually preferred polyfunctional alcohols contain 2 to 100 carbon atoms as for instance polyglycols and polyglycerols.

Gum base polymers may both be resinous and elastomeric polymers.

In the polymerization of a gum base polymer for use in the chewing gum of the present invention, some applicable examples of alcohols, which may be employed as such or as derivatives thereof, include polyols such as ethylene glycol, 1,2-propanediol, 1,3-propanediol, 1,3-butanediol, 1,4-butanediol, 1,6-hexanediol, diethylene glycol, 1,4-cyclohexanediol, 1,4-cyclohexanedimethanol, neopentyl glycol, glycerol, trimethylolpropane, pentaerythritol, sorbitol, mannitol, etc.

Suitable examples of environmentally or biologically degradable chewing gum base polymers, which may be applied in accordance with the gum base of the present invention, include degradable polyesters, polycarbonates, polyester amides, polyesterurethanes, polyamides, prolamine, polypeptides, homopolymers of amino acids such as polylysine, and proteins including derivatives hereof such as e.g. protein hydrolysates including a zein hydrolysate.

Polyesters which may be applied in accordance with the gum base of the present invention may e.g. be as seen in EP 1 545 234 or EP 0 711 506 as incorporated herein by reference.

Further polymers which may be used in the gum base according to embodiments of the invention comprise:
  enzymatically hydrolyzed zein, plasticized poly(D,L-lactic acid) and poly(D,L-lactic acid-co-glycolic acid), polyhydroxyalkanoates having side chain lengths of $C_4$ to $C_{30}$, poly(lactic acid) copolymers selected from the group consisting of poly(lactic acid-dimer fatty acid-oxazoline) copolymers and poly(lactic acid-diol-urethane) copolymers,
  at least one polyester wherein the polyester includes monomers selected from the group consisting of lactic acid, lactide, glycolic acid, glycolide, citric acid, adipic acid, caprolactone, ethylene oxide, ethylene glycol, propylene oxide, and propylene glycol, and combinations thereof,
  at least one polyester that is produced through a reaction of glycerol and at least one acid chosen from the group consisting of citric acid, fumaric acid, adipic acid, malic acid, succinic acid, suberic acid, sebacic acid, dodecanedioic acid, glucaric acid, glutamic acid, glutaric acid, azelaic acid, and tartaric acid,
  at least one polyester that is produced through a reaction of at least one alcohol chosen from the group consisting of glycerol, propylene glycol, and 1,3 butylene diol, and at least one acid chosen from the group consisting of fumaric acid, adipic acid, malic acid, succinic acid, and tartaric acid, the polyester being end-capped with a monofunctional ingredient selected from the group consisting of alcohols, acids, chlorides, and esters,
  and further such as can be found in e.g. U.S. Pat. No. 6,773,730, U.S. Pat. No. 6,613,363, U.S. Pat. No. 6,194,008, U.S. Pat. No. 5,580,590, U.S. Pat. No. 6,858,238, U.S. Pat. No. 6,017,566, U.S. Pat. No. 6,013,287, and U.S. Pat. No. 5,800,848, which are all hereby incorporated by reference.

The polyesters formed on the basis of di- or polyfunctional acids and di- or polyfunctional alcohols may be produced according to known methods, one of which includes US2007/043200, hereby incorporated by reference.

The prolamine may e.g. be selected from the group consisting of zein, corn gluten meal, wheat gluten, gliadin, glutenin and any combination thereof. Methods of providing such a polymer are disclosed in US2004/001903, hereby incorporated by reference.

Examples of such protein based compounds include but are not limited to prolamine, zein, corn gluten meal, wheat gluten, gliadin, glutenin and combinations thereof.

Such suitable biodegradable gum base polymers include polyesters, polycarbonates, polyesteramides, polyesterurethanes, polyamides, prolamine, and combinations thereof.

Carbonates may typically be co-polymerised with esters. Some typically preferred cyclic carbonates, which may be used as starting material, may e.g. comprise trimethylene carbonate, 2,2-dimethyltrimethylene carbonate, 2-methyltrimethylene carbonate, 3-methyltrimethylene carbonate, 2,3-dimethyltrimethylene carbonate, 2,4-dimethyltrimethylene carbonate, 2,3,4-trimethyltrimethylene carbonate, 2,3,3,4-tetramethyltrimethylene carbonate, etc.

In some embodiments, suitable polyesteramides can be constructed from monomers of the following groups: dialcohols, such as ethylene glycol, 1,4-butanediol, 1,3-propanediol, 1,6-hexanediol diethylene glycol and others; and/or dicarboxylic acid, such as oxalic acid, succinic acid, adipic acid and others, including those in the form of their respective esters (methyl, ethyl, etc.); and/or hydroxycarboxylic acids and lactones, such as caprolactone and others; and/or amino alcohols, such as ethanolamine, propanolamine, etc.; and/or cyclic lactams, such as .epsilon.-caprolactam or laurolactam, etc.; and/or .omega.-aminocarboxylic acids, such as aminocaproic acid, etc.; and/or mixtures (1:1 salts) of dicarboxylic acids such as adipic acid, succinic acid etc., and diamines such as hexamethyl enediamine, diaminobutane, etc.

In the case where the polymer mixture is based extensively on thermoplastic starch and an aromatic polyester, an aliphatic-aromatic copolyester, or a polyesteramide, it may be advantageous to add an aliphatic polyester or copolyester, such as polycaprolactone, for example, as a further component. As an example of this there may be mentioned a polymer mixture consisting of thermoplastic starch, at least one polyethylene terephthalate (PET) or a polyalkylene terephthalate, and polycaprolactone. Other examples of aliphatic polyesters or copolyesters are polylactic acid, polyhydroxybutyric acid, polyhydroxybutyric acid-hydroxyvaleric acid copolymer, and/or mixtures thereof.

Suitable polyesters may be obtained through polycondensation polymerisation or ring-opening polymerisation reactions. Some preferred polyesters include those polymerised from at least one carboxylic acid and at least one aliphatic di- or polyfunctional alcohols. The carboxylic acids may include aromatic dicarboxylic acids and aliphatic di- or polyfunctional carboxylic acids. In some preferred embodiments, the majority of the carboxylic acids are aliphatic.

Some of the preferred polyesters according to embodiments of the invention may e.g. be prepared by step-growth polymerization of di-, tri- or higher-functional alcohols or esters thereof with di-, tri- or higher-functional aliphatic or aromatic carboxylic acids or esters thereof. Likewise, also hydroxy acids or anhydrides and halides of polyfunctional carboxylic acids may be used as monomers. The polymerization may involve direct polyesterification or transesterification and may be catalyzed. Use of branched monomers suppresses the crystallinity of the polyester polymers. Mixing of dissimilar monomer units along the chain also suppresses crystallinity. To control the reaction and the molecular weight of the resulting polymer it is possible to stop the polymer chains by addition of monofunctional alcohols or acids and/or to utilize a stoichiometric imbalance between acid groups and alcohol groups or derivatives of either. Also the adding of long chain aliphatic carboxylic acids or aromatic monocarboxylic acids may be used to control the degree of branching in the polymer and conversely multifunctional monomers are sometimes used to create branching. Moreover, following the polymerization monofunctional compounds may be used to end cap the free hydroxyl and carboxyl groups.

Examples of aliphatic di- or polyfunctional carboxylic acids, which may be applied as monomers of suitable polyesters include oxalic, malonic, citric, succinic, malic, tartaric, fumaric, maleic, glutaric, glutamic, adipic, glucaric, pimelic, suberic, azelaic, sebacic, dodecanedioic acid, etc. Likewise, specific examples of aromatic polyfunctional carboxylic acids may be terephthalic, isophthalic, phthalic, trimellitic, pyromellitic and naphthalene 1,4-, 2,3-, 2,6-dicarboxylic acids and the like. Some preferred polyesters are disclosed in CA2523510, hereby included by reference.

In a preferred embodiment, aliphatic dicarboxylic acids applied in the polyesters are selected from aliphatic dicarboxylic acids having from 4 to 12 carbons, such as succinic acid, glutaric acid, 2-methylglutaric acid, 3-methylglutaric acid, 2,2-dimethylglutaric acid, adipic acid, pimelic acid, suberic acid, azelaic acid and sebacic acid, higher homologues and stereoisomers and mixtures thereof. Preferred aliphatic dicarboxylic acids in this embodiment are succinic acid, glutaric acid, adipic acid, pimelic acid, azelaic acid and sebacic acid, and mixtures thereof.

In an embodiment, aromatic dicarboxylic acids applied in the polyesters contain two carboxyl groups which are bound to one aromatic system. Preferably, the aromatic system is carboaromatic, such as phenyl or naphthyl. In the case of polynuclear aromatics, the two carboxyl groups may be bound to the same ring or different rings. The aromatic system can also have one or more alkyl groups, for example methyl groups. The aromatic dicarboxylic acid is then generally selected from aromatic dicarboxylic acids having from 8 to 12 carbons, such as phthalic acid, isophthalic acid, terephthalic acid, 1,5- and 2,6-naphthalenedicarboxylic acid. Preferred aromatic dicarboxylic acids in this embodiment are terephthalic acid, isophthalic acid and phthalic acid and mixtures thereof.

Furthermore, some usually preferred polyfunctional alcohols suitable for preparing advantageous polyesters according to embodiments of the invention contain 2 to 100 carbon atoms as for instance polyglycols and polyglycerols. Suitable examples of alcohols, which may be employed in the polymerization process as such or as derivatives thereof, includes polyols such as ethylene glycol, 1,2-propanediol, 1,3-propanediol, 1,3-butanediol, 1,4-butanediol, 1,6-hexanediol, diethylene glycol, 1,4-cyclohexanediol, 1,4-cyclohexanedimethanol, neopentyl glycol, glycerol, trimethylolpropane, pentaerythritol, sorbitol, mannitol, etc. For the purpose of illustration and not limitation, some examples of alcohol derivatives include triacetin, glycerol palmitate, glycerol sebacate, glycerol adipate, tripropionin, etc.

Additionally, with regard to polyesters polymerized from alcohols or derivatives thereof and carboxylic acids or derivatives thereof, chain-stoppers sometimes used are monofunctional compounds. They are preferably either monohydroxy alcohols containing 1-20 carbon atoms or monocarboxylic acids containing 2-26 carbon atoms. General examples are medium or long-chain fatty alcohols or acids, and specific examples include monohydroxy alcohols such as methanol, ethanol, butanol, hexanol, octanol, etc., and lauryl alcohol, myristyl alcohol, cetyl alcohol, stearyl alcohol, stearic alcohol, etc., and monocarboxylic acids such as acetic, lauric, myristic, palmitic, stearic, arachidic, cerotic, dodecylenic, palmitoleic, oleic, linoleic, linolenic, erucic, benzoic, naphthoic acids and substituted naphthoic acids, 1-methyl-2 naphthoic acid and 2-isopropyl-1-naphthoic acid, etc.

Typically, an acid catalyst or a transesterification catalyst may be used in such polyester polymerization processes, and non-limiting examples of those are the metal catalysts such as acetates of manganese, zinc, calcium, cobalt or magnesium, and antimony(III)oxide, germanium oxide or halide and tetraalkoxygermanium, titanium alkoxide, zinc or aluminum salts.

In a preferred embodiment of the invention, the polyesters can for example include copolymers containing any combination of the monomers lactic acid, lactide, glycolic acid, glycolide, citric acid, adipic acid, caprolactone, ethylene oxide, ethylene glycol, propylene oxide, propylene glycol and combinations thereof.

Examples of suitable polyesters obtainable by ring-opening polymerization include polyesters comprising combinations of cyclic monomers including the following:

D,L-lactide/ε-caprolactone,
D,L-lactide/TMC
D, L-lactide/δ-valerolactone
D, L-lactide/dioxanone
D,L-lactide
L-lactide/ε-caprolactone
L-lactide/TMC
L-lactide/δ-valerolactone
L-lactide/dioxanone
L-lactide
D,L-lactide/glycolide/ε-caprolactone
D,L-lactide/glycolide/TMC
D,L-lactide/glycolide/δ-valerolactone
D,L-lactide/glycolide/dioxanone
D,L-lactide/glycolide
L-lactide/glycolide/ε-caprolactone
L-lactide/glycolide/TMC
L-lactide/glycolide/δ-valerolactone
L-lactide/glycolide/dioxanone
L-lactide/glycolide
glycolide/ε-caprolactone
glycolide/TMC
glycolide/δ-valerolactone
glycolide/dioxanone
glycolide
D, L-lactide/L-lactide/ε-caprolactone
D,L-lactide/L-lactide/TMC
D,L-lactide/L-lactide/δ-valerolactone
D, L-lactide/L-lactide/dioxanone
D, L-lactide/L-lactide
D,L-lactide/L-lactide/glycolide/ε-caprolactone
D,L-lactide/L-lactide/glycolide/TMC
D,L-lactide/L-lactide/glycolide/δ-valerolactone
D,L-lactide/L-lactide/glycolide/dioxanone
D,L-lactide/L-lactide/glycolide Some examples of the resulting polyester gum base polymers include poly(L-lactide-co-trimethylenecarbonate); poly(L-lactide-co-epsilon-caprolactone); poly(D, L-lactide-co-trimethylenecarbonate); poly(D, L-lactide-co-epsilon-caprolactone); poly(meso-lactide-co-trimethylenecarbonate); poly(mesolactide-co-epsilon-caprolactone); poly(glycolide-cotrimethylenecarbonate); poly(glycolide-co-epsilon-caprolactone), etc. suitable polyesters are also disclosed in WO 2004/028270, hereby incorporated by reference.

In an embodiment, the polyesters may be obtained by the reaction between at least one dimer acid and at least one glycol or alcohol. Such glycols can include, for example, glycerin, propylene glycol, ethylene glycol, poly(ethylene glycol), poly(propylene glycol), poly(ethylene glycol-co-propylene glycol), while such alcohols can include, for example, methanol, ethanol, propanol, and butanol, and such dimer acids can include, for example, adipic acid and citric acid, etc.

Some specific examples of suitable polyesters include poly (lactic acid), polylactide, poly(glycolic acid), polyglycolide, poly(citric acid), polycaprolactone, polyhydroxyalkanoate, and combinations thereof.

Some suitable prolamines include zein, corn gluten meal, wheat gluten, gliadin, glutenin and combinations thereof. Moreover, blends of prolamine with polyester such as those disclosed in U.S. Pat. No. 6,858,238, hereby included by reference, may be useful in chewing gum according to embodiments of the invention.

Agglomeration which may be used on e.g. tablet material and active ingredients in an embodiment of the invention may be performed for instance by fluid bed agglomeration, a process known to the person skilled in the art.

The chewing gum may include any component known in the chewing gum art. For example, the chewing gum may include elastomers, bulking agents, waxes, elastomer solvents, emulsifiers, plasticizers, fillers, and mixtures thereof.

The chewing gum according to the invention may comprise coloring agents. According to an embodiment of the invention, the chewing gum may comprise color agents and whiteners such as FD&C-type dyes and lakes, fruit and vegetable extracts, titanium dioxide and combinations thereof.

Further useful chewing gum base components include antioxidants, e.g. butylated hydroxytoluene (BHT), butyl hydroxyanisol (BHA), propylgallate and tocopherols, and preservatives.

A gum base formulation may, in accordance with the present invention, comprise one or more softening agents e.g. sucrose esters including those disclosed in WO 00/25598, which is incorporated herein by reference, tallow, hydrogenated tallow, hydrogenated and partially hydrogenated vegetable oils, cocoa butter, degreased cocoa powder, glycerol monostearate, glyceryl triacetate, lecithin, mono-, di- and triglycerides, acetylated monoglycerides, lanolin, sodium stearate, potassium stearate, glyceryl lecithin, propylene glycol monostearate, glycerine, fatty acids (e.g. stearic, palmitic, oleic and linoleic acids) and combinations thereof. As used herein the term "softener" designates an ingredient, which softens the gum base or chewing gum formulation and encompasses waxes, fats, oils, emulsifiers, surfactants and solubilisers.

To soften the gum base further and to provide it with water-binding properties, which confer to the gum base a pleasant smooth surface and reduce its adhesive properties, one or more emulsifiers is/are usually added to the composition, typically in an amount of 0 to 18% by weight, preferably 0 to 12% by weight of the gum base. Useful emulsifiers can include, but are not limited to, glyceryl monostearate, propylene glycol monostearate, mono- and diglycerides of edible fatty acids, lactic acid esters and acetic acid esters of mono- and diglycerides of edible fatty acids, acetylated mono and diglycerides, sugar esters of edible fatty acids, Na-, K-, Mg- and Ca-stearates, lecithin, hydroxylated lecithin and the like and mixtures thereof are examples of conventionally used emulsifiers which can be added to the chewing gum base. In case of the presence of a biologically or pharmaceutically active ingredient as defined below, the formulation may comprise certain specific emulsifiers and/or solubilisers in order to disperse and release the active ingredient.

Waxes and fats are conventionally used for the adjustment of the texture and for softening of the chewing gum base when preparing chewing gum bases. In connection with the present invention, any conventionally used and suitable type of natural and synthetic wax and fat may be used, such as for instance rice bran wax, polyethylene wax, petroleum wax (refined paraffin and microcrystalline wax), sorbitan monostearate, tallow, propylene glycol, paraffin, beeswax, carnauba wax, candelilla wax, cocoa butter, degreased cocoa powder and any suitable oil or fat, as e.g. completely or partially hydrogenated vegetable oils or completely or partially hydrogenated animal fats.

A chewing gum base formulation may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof.

In addition to a water insoluble gum base portion, a typical chewing gum includes a water soluble bulk portion and one or more flavoring agents. The water-soluble portion may include bulk sweeteners, high-intensity sweeteners, flavoring agents, softeners, emulsifiers, colors, acidulants, buffering agents, fillers, antioxidants, and other components that provide desired attributes.

Combinations of sugar and/or non-sugar sweeteners can be used in the chewing gum formulation processed in accordance with the invention. Additionally, the softener may also provide additional sweetness such as aqueous sugar or alditol solutions.

Useful sugar sweeteners are saccharide-containing components commonly known in the chewing gum art including, but not limited to, sucrose, dextrose, maltose, dextrins, trehalose, D-tagatose, dried invert sugar, fructose, levulose, galactose, corn syrup solids, and the like, alone or in combination.

Sorbitol can be used as a non-sugar sweetener. Other useful non-sugar sweeteners include, but are not limited to, other sugar alcohols such as mannitol, xylitol, hydrogenated starch hydrolysates, maltitol, isomaltol, erythritol, lactitol and the like, alone or in combination.

High-intensity artificial sweetening agents can also be used alone or in combination with the above sweeteners. Preferred high-intensity sweeteners include, but are not limited to sucralose, aspartame, salts of acesulfame, alitame, neotame, twinsweet, saccharin and its salts, cyclamic acid and its salts, glycyrrhizin, dihydrochalcones, thaumatin, monellin, stevioside and the like, alone or in combination. In order to provide longer lasting sweetness and flavor perception, it may be desirable to encapsulate or otherwise control the release of at least a portion of the artificial sweetener. Techniques such as wet granulation, wax granulation, spray drying, spray chilling, fluid bed coating, coascervation, encapsulation in yeast cells and fiber extrusion may be used to achieve the desired release characteristics. Encapsulation of sweetening agents can also be provided using another chewing gum component such as a resinous compound.

Usage level of the high-intensity artificial sweetener will vary considerably and will depend on factors such as potency of the sweetener, rate of release, desired sweetness of the product, level and type of flavor used and cost considerations. Thus, the active level of high-potency artificial sweetener may vary from about 0 to about 8% by weight, preferably 0.001 to about 5% by weight. When carriers used for encapsulation are included, the usage level of the encapsulated sweetener will be proportionately higher.

If a low-calorie gum is desired, a low-caloric bulking agent can be used. Examples of low caloric bulking agents include polydextrose, Raftilose, Raftilin, fructooligosaccharides (NutraFlora®), palatinose oligosaccharides; guar gum hydrolysates (e.g. Sun Fiber®) or indigestible dextrins (e.g. Fibersol®). However, other low-calorie bulking agents can be used.

The chewing gum according to the present invention may contain aroma agents and flavoring agents including natural and synthetic flavorings e.g. in the form of natural vegetable components, essential oils, essences, extracts, powders, including acids and other substances capable of affecting the taste profile. Examples of liquid and powdered flavorings include coconut, coffee, chocolate, vanilla, grape fruit, orange, lime, menthol, liquo-rice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

The chewing gum flavor may be a natural flavoring agent, which is freeze-dried, preferably in the form of a powder, slices or pieces or combinations thereof. The particle size may be less than 3 mm, less than 2 mm or more preferred less than 1 mm, calculated as the longest dimension of the particle. The natural flavoring agent may be in a form where the particle size is from about 3 μm to 2 mm, such as from 4 μm to 1 mm. Preferred natural flavoring agents include seeds from fruit e.g. from strawberry, blackberry and raspberry.

Various synthetic flavors, such as mixed fruit flavors may also be used in the present chewing gum centers. As indicated above, the aroma agent may be used in quantities smaller than those conventionally used. The aroma agents and/or flavors may be used in the amount from 0.01 to about 30% by weight of the final product depending on the desired intensity of the aroma and/or flavor used. Preferably, the content of aroma/flavor is in the range of 0.2 to 5%, more preferably 0.5 to 3%, by weight of the total composition.

In an embodiment of the invention, the flavoring agents comprise natural and synthetic flavorings in the form of natural vegetable components, essential oils, essences, extracts, powders, including acids and other substances capable of affecting the taste profile.

In one embodiment of the invention, the flavor may be used as taste masking in chewing gum comprising active ingredients, which by themselves have undesired taste or which alter the taste of the formulation.

Further chewing gum ingredients, which may be included in the chewing gum according to the present invention, include surfactants and/or solubilisers, especially when pharmaceutically or biologically active ingredients are present. As examples of types of surfactants to be used as solubilisers in a chewing gum composition according to embodiments of the invention, reference is made to H. P. Fiedler, Lexikon der Hilfstoffe für Pharmacie, Kosmetik and Angrenzende Gebiete, pages 63-64 (1981) and the lists of approved food emulsifiers of the individual countries. Anionic, cationic, amphoteric or non-ionic solubilisers can be used. Suitable solubilisers include lecithin, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids and polyoxyethylated hydrogenated castor oil (e.g. the product sold under the trade name CREMOPHOR), block copolymers of ethylene oxide and propylene oxide (e.g. products sold under trade names PLURONIC and POLOXAMER), polyoxyethylene fatty alcohol ethers, polyoxyethylene sorbitan fatty acid esters, sorbitan esters of fatty acids and polyoxyethylene stearic acid esters.

Particularly suitable solubilisers are polyoxyethylene stearates, such as for instance polyoxyethylene(8)stearate and polyoxyethylene(40)stearate, the polyoxyethylene sorbitan fatty acid esters sold under the trade name TWEEN, for instance TWEEN 20 (monolaurate), TWEEN 80 (monooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllatylate, sodium laurylsulfate, polyoxyethylated hydrogenated castor oil, blockcopolymers of ethylene oxide and propyleneoxide and polyoxyethylene fatty alcohol ether. The solubiliser may either be a single compound or a combination of several compounds. In the presence of an active ingredient, the chewing gum may preferably also comprise a carrier known in the art.

Active ingredients may advantageously be applied in a chewing gum according to the invention. Active ingredients generally refer to those ingredients that are included in a delivery system and/or compressible chewing gum composition for the desired end benefit they provide to the user. In some embodiments, active ingredients can include medicaments, nutrients, nutraceuticals, herbals, nutritional supplements, pharmaceuticals, drugs, and the like and combinations thereof. Moreover, in the present context, active ingredients may refer to flavor components, high intensity sweeteners or other taste establishing components.

Preferred API to be used in compressed chewing gum tablets according to embodiments of the invention are selected from the groups of antihistamines, anti-smoking agents, agents used for diabetes, decongestants, peptides, pain-relieving agents, antacids, nausea-relieving agents, statines, and other.

Most preferred API according to embodiments of the invention are cetirizine, levo cetirizine, nicotine, nicotine polacrilex, nicotine in combination with alkaline agents, metformin, metformin HCL, phenylephrine, GLP-1, exenatide, deca-peptide, KSL-W (acetate), fluor, and chlorhexidine.

Also preferred API according to embodiments of the invention are loratadine, des-loratadine, nicotine bitartrate, nicotine in combination with caffeine, nicotine antagonists, combinations thereof or compounds comprising one or more of these, pseudoephedrine, flurbiprofen, paracetamol, acetylsalicylic acid, Ibuprofen, antacida, cimetidine, ranitidine, ondansetron, granisetron, metoclopramid, simvastatin, lovastatin, fluvastatin, acyclovir, benzydamin, rimonabant, varenicline, sildenafil, naltrexone, fluor in combination with fruit acids, derivatives, salts or isomers of chlorhexidine.

Some groups of suitable enhancers to e.g. enhance the uptake of API include bile salts, cetomacrogols, chelating agents, citrates, cyclodextrins, detergents, enamine derivatives, fatty acids, labrasol, lecithins, phospholipids, synthetic and natural surfactants, nonionic surfactants, cell envelope disordering compounds, solvents, steroidal detergents, chelators, solubilization agents, charge modifying agents, pH control agents, degradative enzyme inhibitors, and mucolytic or mucus clearing agents.

Further groups of suitable enhancers include modulatory agents of epithelial junction physiology such as nitric oxide (NO) stimulators, chitosan, and chitosan derivatives; and vasodilator agents, selective transport-enhancing agents, stabilizing delivery vehicles, carriers, supports or complex-forming species with which exendins may be effectively combined, associated, contained, encapsulated or bound to stabilize an active agent for enhanced mucosal delivery; and membrane penetration-enhancing agents including surfactants, bile salts, phospholipid or fatty acid additives, mixed micelle, liposome, carrier, alcohol, enamine, NO donor compound, a long-chain amphipathic molecule, small hydrophobic penetration enhancer, sodium or a salicylic acid derivative, glycerol ester of acetoacetic acid, cyclodextrin or beta-cyclodextrin derivative, medium-chain fatty acid, chelating agent, amino acid or salt thereof, N-acetylamino acid or salt thereof, enzyme degradative to a selected membrane component, inhibitor of fatty acid synthesis, inhibitor of cholesterol synthesis, any combination of the membrane penetration enhancing agents.

Examples of enhancers suitable for application in compressed chewing gum tablets according to embodiments of the invention include cetylpyridinium chloride (CPC), benzalkonium chloride, sodium lauryl sulfate, polysorbate 80, Polysorbate 20, cetyltrimethylammonium bromide, laureth 9, sodium salicylate, sodium EDTA, EDTA, aprotinin, sodium taurocholate, saponins, bile salt derivatives, fatty acids, sucrose esters, azone emulsion, dextran sulphate, linoleic acid, labrafil, transcutol, urea, azone, nonionic surfactants, sulfoxides, sauric acid/PG, POE 23 lauryl ether, methoxysalicylate, dextran sulfate, methanol, ethanol, sodium cholate, Sodium taurocholate, Lysophosphatidyl choline, Alkylglycosides, polysorbates, Sorbitan esters, Poloxamer block copolymers, PEG-35 castor oil, PEG-40 hydrogenated castor oil, Caprocaproyl macrogol-8 glycerides, PEG-8 caprylic/capric, glycerides, Dioctyl sulfosuccinate, Polyethylene lauryl ether, Ethoxydiglycol, Propylene glycol, mono-di-caprylate, Glycerol monocaprylate, Glyceryl fatty acids ($C_8$-$C_{18}$) ethoxylated.

Oleic acid, Linoleic acid, Glyceryl caprylate/caprate, Glyceryl monooleate, Glyceryl monolaurate, Capryliccapric triglycerides, Ethoxylated nonylphenols, PEG-(8-50) stearates, Olive oil PEG-6, esters, Triolein PEG-6 esters, Lecithin, d-alpha tocopherol polyethylene glycol 1,000 succinate, Citric acid, Sodium citrate, BRIJ, Sodium laurate, 5-methoxysalicylic acid, Bile salts, Acetyl salicylate, ZOT, Docosahexaenoic acid, Alkylglycosides, Sodium glycocholate (GC-Na), Sodium taurocholate (TC-Na), EDTA, Choline salicylate, Sodium caprate (Cap-Na), N-lauryl-beta-D-maltopyranoside (LM), Diethyl maleate, Labrasol, Sodium salicylate, Mentol, Alkali metal alkyl sulphate, Sodium lauryl sulphate, Glycerin, Bile acid, Lecithin, phosphatidylcholine, phosphatidylserine, sphingomyelin, phosphatidylethanolamine, cephalin, lysolecithin, Hyaluronic acid: alkalimetal salts, sodium, alkaline earth and aluminum, Octylphenoxypolyethoxyethanol, Glycolic acid, Lactic acid, Chamomile extract, Cucumber extract, Borage oil (Hjulkrone olie), Evening primrose oil, Polyglycerin, Lysine, Polylysine, Triolein, Monoolein, Monooleates, Monolaurates, Polydocanol alkyl ethers, Chenodeoxycholate, Deoxycholate, Glycocholic acid, Taurocholic acid, Glycodeoxycholic acid, Taurodeoxycholic acid, Sodium glycocholate, Phosphatidylcholine, Phosphatidylserine, Sphingomyelin, Phosphatidylethanolamine, Cephalin, Lysolecithin, Alkali metal hyaluronates, Chitosan, Poly-L-arginine, Alkyl glucoside, Saccharide alkyl ester, Fusidic acid derivatives, Sodium taurdihydrofusidate (STDHF), L-α-phosphatidylcholine Didecanoyl (DDPC), Nitroglycerine, nitropruside, NOC5 [3-(2-hydroxy-1-(methyl-ethyl)-2-nitrosohydrazino)-1-propanamine], NOC12 [iV-ethyl-2-(l-ethyl-hydroxy-2-nitrosohydrazino)-ethanamine, SNAP [S-nitroso-N-acetyl-DLpenicillamine, NORI, NOR4, deacylmethyl sulfoxide, azone, salicylamide, glyceryl-l,3-diacetoacetate, 1,2-isopropylideneglycerine-3-acetoacetate), Amino acids, Amino acid salts, monoaminocarboxlic acids, Glycine, alanine, phenylalanine, proline, hydroxyproline, hydroxyamino acids, serine, acidic amino acids, aspartic acid, Glutamic acid, Basic amino acids, Lysine, N-acetylamino acids, N-acetylalanine, N-acetylphenylalanine, TM-acetylserine, N-acetylglycine, N-acetyllysine, N-acetylglutamic acid, N-acetylproline, N-acetylhydroxyproline, lactic acid, malic acid and citric acid and alkali metal salts thereof, pyrrolidonecarboxylic acids, alkylpyrrolidonecarboxylic acid esters, N-alkylpyrrolidones, proline acyl esters, sodium lauryl phosphate, sodium lauryl sulphate, sodium oleyl phosphate, sodium myristyl sulphate, polyoxyethylene alkyl ethers, polyoxyethylene alkyl esters, caproic acid, alkylsaccharide, fusidic acid, polyethylene glycol, cetyl alcohol, polyvinylpyrolidone, Polyvinyl alcohol, Lanolin alcohol, Sorbitan monooleate, Ethylene glycol tetraacetic acid, Bile acid conjugate with taurine, Cholanic acid and salts, Cyclodextran, Cyclodextrin, Cyclodextrin (beta), Hydroxypropyl-β-cyclodextran, Sulfobutylether-β-cyclodextran, Methyl-β-cyclodextrin, Chitosan glutamate, Chitosan acetate, Chitosan hydrochloride, Chitosan hydrolactate, 1-O-alkyl-2-hydroxy-sn-glycero-3-phosphocholine, 3-O-alkyl-2-acetoyl-sn-glycero-1-phosphocholine, 1-O-alkyl-2-O-acetyl-sn-glycero-3-phospho(N,N,N-trimethyl)hexanolamine, propylene glycol, tetradecylmaltoside (TDM), sucrose dedecanoate.

Examples of suitable mucoadhesives as enhancers according to the invention include Carbopol 934+HPC, Maize+ Carbopol 907, HPC (hydroxypropyl cellulose), Na-CMC, HPMC (hydroxypropylmethylcellulose), HEMA hydroxyethyl metacrylate, Carbopol 907 crosslinked with sucrose, Polyacrylic acids (PAA), Chitosans, Lectins, Polymetacrylate derivatives, Hyaluronic acid, P(AA-co-PEG) monomethylether monomethacrylate, PAA-PVP (Poly acrylic acid-poly vinyl pyrrilidone), PVP-PEG, methylcellulose, N-Trimethyl Chitosans, PDMAEMA, poly(dimethyl-aminoethyl methacrylate), HEC Hydroxyethyl Cellulose, Carbomer 940, Carbomer 971, Polyethylene Oxide, Dextrin, Poly(Methyl Vinyl Ether/Maleic Anhydride), Polycarbophil that is polymers of acrylic acid crosslinked with divinyl glycol, PVP (PVP: Poly vinyl pyrrilidone), Agar, Tragacanth, Sodium Alginate, Karaya gum, MEC, HPC(HPC: Hydroxy propyl cellulose), Lectins, AB Block copolymer of oligo (methyl methacrylate) and PAA, Polymers with thiol groups, Spheromers, Thiomers, Alginic acid sodium salt, Carbopol 974P (Carbomer), EC (EC: Ethylcellulose), CMC (CMC: Carboxymethyl cellulose), Dextran, Guar Gum, Pectins, Starch, Gelatin, Casein, Acrylic acid polymers, Polymers of acrylic acid esters, Acrylic acid copolymers, Vinyl polymers, Vinyl copolymers, Polymers of Vinyl alcohols, Alcoxy polymers, polyethylene oxide polymers, and polyethers.

Some groups of suitable enhancers for application according to embodiments of the invention include solubilization agents; charge modifying agents; pH control agents; degradative enzyme inhibitors; modulatory agents of epithelial junction physiology, such as nitric oxide (NO) stimulators, chitosan, or chitosan derivatives; vasodilator agents; selective transport-enhancing agents; stabilizing delivery vehicles, carriers, supports or complex-forming species with which exendin(s) is/are effectively combined, associated, contained, encapsulated or bound to stabilize the active agent for enhanced mucosal delivery; small hydrophilic penetration enhancers; emulsifiers, mucolytic or mucus clearing agents; membrane penetration-enhancing agents such as e.g., (i) a surfactant, (ii) a bile salt, (iii) a phospholipid or fatty acid additive, mixed micelle, liposome, or carrier, (iv) an alcohol, (v) an enamine, (iv) an NO donor compound, (vii) a long-chain amphipathic molecule, (viii) a small hydrophobic penetration enhancer, (ix) sodium or a salicylic acid derivative, (x) a glycerol ester of acetoacetic acid, (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, (xviii) an inhibitor of cholesterol synthesis; or (xiv) any combination of the membrane penetration enhancing agents of (i)-(xviii)).

In various embodiments of the invention, exendin is combined with one, two, three, four or more of the mucosal delivery-enhancing agents recited above.

Some suitable enhancers for application according to the present invention are pH control agents selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

The suitable pH control agents suitable according to the present invention include buffers.

Examples of dry binders to be used according to embodiments of the invention include mikro-crystalline cellulose (MCC), silicified micro-crystalline cellulose (SMCC), spray dried lactose, fast flow lactose, anhydrous lactose, sucrose, mannitol, mannitol EZ, dextrose, fructose, sorbitol, povidone, copovidone, dicalcium phosphate (DCP), starch (corn, potato and rice), pre-gelatinized starch, or combinations thereof. A number of filler materials may furthermore be used as dry binders.

Active ingredients may be classified according to The Anatomical Therapeutic Chemical (ATC) classification system, which is a system for classification of medicinal products according to their primary constituent and to the organ or system on which they act and their chemical, pharmacological and therapeutic properties.

The first level of the ATC is split into 14 main groups based on the anatomical group:

A: Alimentary tract and metabolism
B: Blood and blood forming organs
C: Cardiovascular system
D: Dermatologicals
G: Genito urinary system and sex hormones
H: Systemic hormonal preparations, excl. sex hormones and insulins
J: Antiinfectives for systemic use
L: Antineoplastic and immunomodulating agents
M: Musculo-skeletal system
N: Nervous system
P: Antiparasitic products, insecticides and repellents
R: Respiratory system
S: Sensory organs
V: Various Further subdivision is done into a second, third, fourth and fifth sub-group, which is based on the therapeutic main group, the therapeutic/pharmacological subgroup, the chemical/therapeutic/pharmacological subgroup, and the chemical substance subgroup respectively. In this sense each active ingredient has been given a unique ATC identification code indicating where the active ingredient may be useful.

However, as some active ingredients are useful in more than one area, some of the active ingredients mentioned in this document belong to two or more of the mentioned groups, e.g. phenylephrine, which has an ATC identification code in both C, R, and S, i.e. both C01CA06, R01AA04, R01AB01, R01BA03, S01FB01, and S01GA05 are ATC identification codes identifying phenylephrine.

The following list discloses examples of active ingredients which can be classified according to the ATC classification mentioned above and which are active ingredients which may be used in a compressed chewing gum according to embodiments of the invention:

Ephedrine, Magaldrate, Pseudoephedrine, Sildenafil, Xylocaine, Benzalconium chloride, Caffeine, Phenylephrine, Amfepramone, Orlistat, Sibutramine, Acetaminophen, Aspirin, Aluminum amino acetate, Aluminum amino acetate in combination with Magnesium oxide, Aluminum oxide hydrate in combination with Magnesiumoxide, Calcium carbonate in combination with Magnesium hydroxide, Calciumcarbonate, Dihydroxy Aluminum sodium carbonate, Magnesiumoxide, Glitazones, Metformin, Chlorpromazine, Dimenhydrinat, Domperidone, Meclozine, Metoclopramide, Odansetron, Prednisolone, Promethazine, Acrivastine, Cetirizine, Cinnarizine, Clemastine, Cyclizine, Desloratadine, Dexchlorpheniramine, Dimenhydrinate, Ebastine, Fexofenadine, Ibuprofen, Levolevoproricin, Loratadine, Meclozine, Mizolastine, Promethazine, Miconazole, Vitamin B12, Folic acid, Ferro compounds, vitamin C, Chlorhexidine diacetate, Fluoride, Decapeptide KSL, Aluminum fluoride, Aminochelated calcium, Ammonium fluoride, Ammonium fluorosilicate, Ammonium monofluorophosphate, Calcium fluoride, Calcium gluconate, Calcium glycerophosphate, Calcium lactate, Calcium monofluorophosphate, Calciumcarbonate, Carbamide, Cetyl pyridinium chloride, Chlorhexidine, Chlorhexidine digluconate, Chlorhexidine Chloride, Chlorhexidine diacetate, CPP Caseine Phospho Peptide, Hexetedine, Octadecentyl Ammonium fluoride, Potassium fluorosilicate, Potassium Chloride, Potassium monofluorophosphate, Sodium bi carbonate, Sodium carbonate, Sodium fluoride, Sodium fluorosilicate, Sodium monofluorophosphate, Sodium tri polyphosphate, Stannous fluoride, Stearyl Trihydroxyethyl Propylenediamine Dihydrofluoride, Strontium chloride, Tetra potassium pyrophosphate, Tetra sodium pyrophosphate, Tripotassium orthophosphate, Trisodium orthophosphate, Alginic acid, Aluminum hydroxide, Sodium bicarbonate, Sildenafil, Tadalafil, Vardenafil, Yohimbine, Cimetidine, Nizatidine, Ranitidine, Acetylsalicylic acid, Clopidogrel, Acetylcysteine, Bromhexine, Codeine, Dextromethorphan, Diphenhydramine, Noscapine, Phenylpropanolamine, vitamin D, Simvastatin, Bisacodyl, Lactitol, Lactulose, Magnesium oxide, Sodium picosulfate, Senna glycosides, Benzocaine, Lidocaine, Tetracaine, Almotriptan, Eletriptan, Naratriptan, Rizatriptan, Sumatriptan, Zolmitriptan, Calcium, Chromium, Copper, Iodine, Iron, Magnesium, Manganese, Molybdenum, Phosphor, Selenium, Zinc, Nicotine, Nicotine bitartrate, Nicotine pftalate, Nicotine polacrilex, Nicotine sulphate, Nicotine tartrate, Nicotine citrate, Nicotine lactate, Chloramine, Hydrogenperoxide, Metronidazole, Triamcinolonacetonide, Benzethonium Chl., Cetyl pyrid. Chl., Chlorhexidine, Fluoride, Lidocaine, Amphotericin, Miconazole, Nystatin, Fish oil, Ginkgo Biloba, Ginseng, Ginger, Purple coneflower, Saw Palmetto, Cetirizine, Levocetirizine, Loratadine, Diclofenac, Flurbiprofen, Acrivastine Pseudoephedrine, Loratadine Pseudoephedrine, Glucosamine, hyaluronic acid, Decapeptide KSL-W, Decapeptide KSL, Resveratrol, Misoprostol, Bupropion, Nicotine, Ondansetron HCl, Esomeprazole, Lansoprazole, Omeprazole, Pantoprazole, Rabeprazole, Bacteria and the like, Loperamide, Simethicone, Acetylsalicylic acid and others, Sucralfate, Vitamin A, Vitamin B1, Vitamin B12, Vitamin B2, Vitamin B6, Biotin, Vitamin C, Vitamin D, Vitamin E, Folinic acid, Vitamin K, Niacin, Q10, Clotrimazole, Fluconazole, Itraconazole, Ketoconazole, Terbinafine, Allopurinol, Probenecid, Atorvastatin, Fluvastatin, Lovastatin, Nicotinic acid, Pravastatin, Rosuvastatin, Simvastatin, Pilocarpine, Naproxen, Alendronate, Etidronate, Raloxifene, Risedronate, Benzodiazepines, Disulfuram, Naltrexone, Buprenorphine, Codeine, Dextropropoxyphene, Fentanyl, Hydromorphone, Ketobemidone, Ketoprofen, Methadone, Morphine, Naproxen, Nicomorphine, Oxycodone, Pethidine, Tramadol, Amoxicillin, Ampicillin, Azithromycin, Ciprofloxacin, Clarithromycin, Doxycyclin, Erythromycin, Fusidic acid, Lymecycline, Metronidazole, Moxifloxacin, Ofloxacin, Oxytetracycline, Phenoxymethylpenicillin, Rifamycins, Roxithromycin, Sulfamethizole, Tetracycline, Trimethoprim, Vancomycin, Acarbose, Glibenclamide, Gliclazide, Glimepiride, Glipizide, Insulin, Repaglinide, Tolbutamide, Oseltamivir, Aciclovir, Famciclovir, Penciclovir, Valganciclovir, Amlopidine, Diltiazem, Felodipine, Nifedipine, Verapamil, Finasteride, Minoxidil, Cocaine, Buphrenorphin, Clonidine, Methadone, Naltrexone, Calciumantagonists, Clonidine, Ergotamine, β-blockers, Aceclofenac, Celecoxib, Dexiprofen, Etodolac, Indometacin, Ketoprofen, Ketorolac, Lornoxicam, Meloxicam, Nabumetone, Oiroxicam, Parecoxib, Phenylbutazone, Piroxicam, Tiaprofenic acid, Tolfenamic acid, Aripiprazole, Chlorpromazine, Chlorprothixene, Clozapine, Flupentixol, Fluphenazine, Haloperidol, Lithium carbonate, Lithium citrate, Melperone, Penfluridol, Periciazine, Perphenazine, Pimozide, Pipamperone, Prochlorperazine, Risperidone, Thioridizin, Fluconazole, Itraconazole, Ketoconazole, Voriconazole, Opium, Benzodiazepines, Hydroxine, Meprobamate, Phenothiazine, Aluminumaminoacetate, Esomeprazole, Famotidine, Magnesium oxide, Nizatide, Omeprazole, Pantoprazole, Fluconazole, Itraconazole, Ketoconazole, Metronidazole, Amphetamine, Atenolol, Bisoprolol fumarate, Metoprolol, Metropolol, Pindolol, Propranolol, Auranofin, and Bendazac.

Further examples of useful active ingredients include active ingredients selected from the therapeutical groups comprising: Analgesic, Anaestetic, Antipyretic, Anti allergic, Anti-arrhythmic, Appetite suppressant, Antifungal, Anti-inflammatory, Broncho dilator, Cardiovascular drugs, Coronary dilator, Cerebral dilator, Peripheral vasodilator, Anti-infective, Psychotropic, Anti-manic, Stimulant, Antihistamine, Laxative, Decongestrant, Gastro-intestinal sedative, Sexual dysfunction agent, Desinfectants, Anti-diarrheal, Anti-anginal substance, Vasodilator, Anti-hypertensive agent, Vasoconstrictor, Migraine treating agent, Antibiotic, Tranquilizer, Ntipsychotic, Anti-tumor drug, Anticoagulant, Antithrombotic agent, Hypnotic, Sedative, Anti-emetic, Anti-, auseant, Anticonvulsant, Neuromuscular agent, Hyper and hypoglycaemic, Thyroid and antithyroid, Diuretic, Antispasmodic, Uterine relaxant, Anti-obesity agent, Anoretic, Spasnolytics, Anabolic agent, Erythropoietic agent, Anti-asthmatic, Expectorant, Cough suppressant, Mucolytic, Anti-uricemic agent, Dental vehicle, Breath freshener, Antacid, Anti-diuretc, Anti-flatulent, Betablokker, Teeth Whitener, Enzyme, Co-enzyme, Protein, Energy booster, Fiber, Probiotics, Prebiotics, Antimicrobial agent, NSAID, Anti-tussives, Decongestrants, Anti-histamines, Expectorants, Anti-diarrheals, Hydrogen antagonists, Proton pump inhibitors, General nonselective CNS depressants, General nonselective CNS stimulants, Selectively CNS function modifying drugs, Antiparkinsonism, Narcotic-analgetics, Analgetic-antipyretics, Psychopharmacological drugs, and Sexual dysfunction agents.

Examples of useful active ingredients include: Casein glyco-macro-peptide (CGMP), Nicotine, Nicotine bitartrate, Nicotine sulphate, Nicotine tartrate, Nicotine pftalate, Nicotine lactate, Nicotinecitrate, Nicotine polacrilex, Triclosan, Cetyl pyridinium chloride, Domiphen bromide, Quarternary ammonium salts, Zinc components, Sanguinarine, Fluorides, Alexidine, Octonidine, EDTA, Aspirin, Acetaminophen, Ibuprofen, Ketoprofen, Diflunisal, Fenoprofen calcium, Naproxen, Tolmetin sodium, Indomethacin, Benzonatate, Caramiphen edisylate, Menthol, Dextromethorphan hydrobromide, Theobromine hydrochloride, Chlophendianol Hydrochloride, Pseudoephedrine Hydrochloride, Phenylephrine, Phenylpropanolamine, Pseudoephedrine sulphate, Brompheniramine maleate, Chlorpheniramine-maleate, Carbinoxamine maleate, Clemastine fumarate, Dexchlorpheniramine maleate, Dephenhydramine hydrochloride, Diphenpyralide hydrochloride, Azatadine maleate, Diphenhydramine citrate, Doxylamine succinate, Promethazine hydrochloride, Pyrilamine maleate, Tripellenamine citrate, Triprolidine hydrochloride, Acrivastine, Loratadine, Brompheniramine, Dexbrompheniamine, Guaifenesin, Ipecac, Potassium iodide, Terpin hydrate, Loperamide, Famotidine, Ranitidine, Omeprazole, Lansoprazole, Aliphatic alcohols, Barbiturates, Caffeine, Nicotine, Strychnine, Picrotoxin, Pentyenetetrazol, Phenylhydantoin, Phenobarbital, Primidone, Carbamazapine, Etoxsuximide, Methsuximide, Phensuximide, Trimethadione, Diazepam, Benzodiazepines, Phenacemide, Pheneturide, Acetazolamide, Sulthiame, Bromide, Levodopa, Amantadine, Morphine, Heroin, Hydromorphone, Metopon, Oxymorphone, Levophanol, Codeine, Hydrocodone, Xycodone, Nalorphine, Naloxone, Naltrexone, Salicylates, Phenylbutazone, Indomethacin, Phenacetin, Chlorpromazine, Methotrimeprazine, Haloperidol, Clozapine, Reserpine, Imipramine, Tranylcypromine, Phenelzine, Lithium, Sildenafil citrate, Tadalafil, and Vardenafil CL.

Examples of useful active ingredients include active ingredients selected from the groups of ace-inhibitors, antianginal drugs, anti-arrhythmias, anti-asthmatics, anti-cholesterolemics, analgesics, anesthetics, anticonvulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplasties, antiparkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocriptine or nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of active ingredients contemplated for use in the present invention can include antacids, H2-antagonists, and analgesics. For example, antacid dosages can be prepared using the ingredients calcium carbonate alone or in combination with magnesium hydroxide, and/or aluminum hydroxide. Moreover, antacids can be used in combination with H2-antagonists.

Analgesics include opiates and opiate derivatives, such as Oxycontin™, ibuprofen, aspirin, acetaminophen, and combinations thereof that may optionally include caffeine.

Other drug active ingredients for use in embodiments can include anti-diarrheals such as Immodium™ AD, anti-histamines, anti-tussives, decongestants, vitamins, and breath fresheners. Also contemplated for use herein are anxiolytics such as Xanax™; anti-psychotics such as Clozaril™ and Haldol™; non-steroidal anti-inflammatories (NSAID's) such as ibuprofen, naproxen sodium, Voltaren™ and Lodine™, anti-histamines such as Claritin™, Hismanal™, Relafen™, and Tavist™; antiemetics such as Kytril™ and Cesamet™; bronchodilators such as Bentolin™, Proventil™; anti-depressants such as Prozac™, Zoloft™, and Paxil™; anti-migraines such as Imigra™, ACE-inhibitors such as Vasotec™, Capoten™ and Zestril™; anti-Alzheimer's agents, such as Nicergoline™, and CaH-antagonists such as Procardia™, Adalat™, and Calan™.

The popular H2-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients can include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts. A variety of nutritional supplements may also be used as active ingredients including virtually any vitamin or mineral. For example, vitamin A, vitamin C, vitamin D, vitamin E, vitamin K, vitamin B6, vitamin B12, thiamine, riboflavin, biotin, folic acid, niacin, pantothenic acid, sodium, potassium, calcium, magnesium, phosphorus, sulfur, chlorine, iron, copper, iodine, zinc, selenium, manganese, choline, chromium, molybdenum, fluorine, cobalt and combinations thereof, may be used. Examples of nutritional supplements that can be used as active ingredients are set forth in U.S. Patent Application Publication Nos. 2003/0157213 AI, 2003/0206993 and 2003/0099741 AI which are incorporated in their entirety herein by reference for all purposes. Various herbals may also be used as active ingredients such as those with various medicinal or dietary supplement properties. Herbals are generally aromatic plants or plant parts and or extracts thereof that can be used medicinally or for flavoring. Suitable herbals can be used singly or in various mixtures. Commonly used herbs include Echinacea, Goldenseal, Calendula, Rosemary, Thyme, Kava Kava, Aloe, Blood Root, Grapefruit Seed Extract, Black Cohosh, Ginseng, Guarana, Cranberry, Ginko Biloba, St. John's Wort, Evening Primrose Oil, Yohimbe Bark, Green Tea, Ma Huang, Maca, Bilberry, Lutein, and combinations thereof.

Especially when hydrophilic, encapsulation of the active ingredient will result in a delay in the release of the predominant amount of the active ingredient during consumption of a compressible chewing gum that includes the encapsulated active ingredient (e.g., as part of a delivery system added as an ingredient to the compressible chewing gum), in some embodiments, the release profile of the ingredient (e.g., the active ingredient) can be managed for a compressible gum by managing various characteristics of the ingredient, delivery system containing the ingredient, and/or the compressible chewing gum containing the delivery system and/or how the delivery system is made. For example, characteristics may include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the compressible chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, the release profiles of one or more components of an effervescing system are managed for a compressible gum. The effervescent system may include one or more edible acids and one or more edible alkaline materials. The edible acid(s) and the edible alkaline material(s) may react together to generate effervescence. In some embodiments, the alkaline material(s) may be selected from, but is not limited to, alkali metal carbonates, alkali metal bicarbonates, alkaline earth metal carbonates, alkaline earth metal bicarbonates, and combinations thereof. The edible acid(s) may be selected from, but is not limited to, citric acid, phosphoric acid, tartaric acid, malic acid, ascorbic acid, and combinations thereof. In some embodiments, an effervescing system may include one or more other ingredients such as, for example, carbon dioxide, oral care ingredients, flavorants, etc.

For examples of use of an effervescing system in a chewing gum, refer to U.S. Provisional Patent No. 60/618,222 filed Oct. 13, 2004, and entitled "Effervescent Pressed Gum Tablet Compositions," the contents of which are incorporated herein by reference for all purposes. Other examples can be found in U.S. Pat. No. 6,235,318, the contents of which are incorporated herein by reference for all purposes. Typically, encapsulation of the one or more ingredients in an effervescing system will result in a delay in the release of the predominant amount of the one or more ingredients during consumption of a compressible chewing gum that includes the encapsulated one or more ingredients (e.g., as part of a delivery system added as an ingredient to the compressible chewing gum composition). The release profile of the one or more ingredients can be managed for a compressible gum by managing various characteristics of the ingredient, delivery system containing the ingredient, and/or the compressible chewing gum containing the delivery system and/or how the delivery system is made. For example, characteristics may include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the compressible chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, the release profiles of one or more appetite suppressors are managed for a compressible gum. Appetite suppressors can be ingredients such as fiber and protein that function to depress the desire to consume food. Appetite suppressors can also include benzphetamine, diethylpropion, mazindol, phendimetrazine, phentermine, hoodia (P57), Olibra™, ephedra, caffeine and combinations thereof. Appetite suppressors are also known by the following trade names: Adipex™, Adipost™, Bontril™ PDM, Bontril™ Slow Release, Didrex™, Fastin™, Ionamin™, Mazanor™, Melfiat™, Obenix™, Phendiet™, Phendiet-105™, Phentercot™, Phentride™, Plegine™, Prelu-2™, Pro-Fast™, PT 105™, Sanorex™, Tenuate™, Sanorex™, Tenuate™, Tenuate Dospan™, Tepanil Ten-Tab™, Teramine™, and Zantryl™. These and other suitable appetite suppressors are further described in the following U.S. patents, all of which are incorporated in their entirety by reference hereto: U.S. Pat. No. 6,838,431 to Portman, U.S. Pat. No. 6,716,815 to Portman, U.S. Pat. No. 6,558,690 to Portman, U.S. Pat. No. 6,468,962 to Portman, U.S. Pat. No. 6,436,899 to Portman.

Typically, encapsulation of the appetite suppressor will result in a delay in the release of the predominant amount of the appetite suppressor during consumption of a compressible chewing gum that includes the encapsulated appetite suppressor (e.g., as part of a delivery system added as an ingredient to the compressible chewing gum). In some embodiments, the release profile of the ingredient (e.g., the appetite suppressor) can be managed for a compressible gum by managing various characteristics of the ingredient, delivery system containing the ingredient, and/or the compressible chewing gum containing the delivery system and/or how the delivery system is made. For example, characteristics may include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the compressible chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, the release profiles of one or more breath fresheners are managed for a compressible gum. Breath fresheners can include essential oils as well as various aldehydes, alcohols, and similar materials. In some embodiments, essential oils can include oils of spearmint, peppermint, wintergreen, sassafras, chlorophyll, citral, geraniol, cardamom, clove, sage, carvacrol, eucalyptus, cardamom, magnolia bark extract, marjoram, cinnamon, lemon, lime, grapefruit, and orange. In some embodiments, aldehydes such as cinnamic aldehyde and salicylaldehyde can be used. Additionally, chemicals such as menthol, carvone, iso-garrigol, and anethole can function as breath fresheners. Of these, the most commonly employed are oils of peppermint, spearmint and chlorophyll.

In addition to essential oils and chemicals derived from them, in some embodiments, breath fresheners can include but are not limited to zinc citrate, zinc acetate, zinc fluoride, zinc ammonium sulfate, zinc bromide, zinc iodide, zinc chloride, zinc nitrate, zinc fluorosilicate, zinc gluconate, zinc tartarate, zinc succinate, zinc formate, zinc chromate, zinc phenol sulfonate, zinc dithionate, zinc sulfate, silver nitrate, zinc salicylate, zinc glycerophosphate, copper nitrate, chlorophyll, copper chlorophyll, chlorophyllin, hydrogenated cottonseed oil, chlorine dioxide, beta cyclodextrin, zeolite, silica-based materials, carbon-based materials, enzymes such as laccase, and combinations thereof. In some embodiments, the release profiles of probiotics can be managed for a compressible gum including, but not limited to lactic acid producing microorganisms such as *Bacillus coagulans, Bacillus subtilis, Bacillus laterosporus, Bacillus laevolacticus, Sporolactobacillus inulinus, Lactobacillus acidophilus, Lactobacillus curvatus, Lactobacillus plantarum, Lactobacillus jenseni, Lactobacillus casei, Lactobacillus fermentum, Lactococcus lactis, Pedioccocus acidilacti, Pedioccocus pentosaceus, Pedioccocus urinae, Leuconostoc mesenteroides, Bacillus coagulans, Bacillus subtilis, Bacillus laterosporus, Bacillus laevolacticus, Sporolactobacillus inulinus* and mixtures thereof. Breath fresheners are also known by the following trade names: Retsyn™, Actizol™, and Nutrazin™. Examples of malodor-controlling compositions are also included in U.S. Pat. No. 5,300,305 to Stapler et al. and in U.S. Patent Application Publication Nos. 2003/0215417 and 2004/0081713 which are incorporated in their entirety herein by reference for all purposes.

Typically, encapsulation of the breath-freshening ingredient will result in a delay in the release of the predominant amount of the active ingredient during consumption of a compressible chewing gum that includes the encapsulated breath-freshening ingredient (e.g., as part of a delivery system added as an ingredient to the compressible chewing gum composition). In some embodiments, the release profile of the ingredient (e.g., the breath-freshening ingredient) can be managed for a compressible gum by managing various characteristics of the ingredient, delivery system containing the ingredient, and/or the compressible chewing gum containing the delivery system and/or how the delivery system is made. For example, characteristics may include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the compressible chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, the release profiles of one or more dental care ingredients may be managed for a compressible gum. Such dental care ingredients (also known as oral care ingredients) may include but are not limited to tooth whiteners, stain removers, oral cleaning, bleaching agents, desensitizing agents, dental remineralization agents, antibacterial agents, anticaries agents, plaque acid buffering agents, surfactants and anticalculus agents. Non-limiting examples of such ingredients can include, hydrolytic agents including proteolytic enzymes, abrasives such as hydrated silica, calcium carbonate, sodium bicarbonate and alumina, other active stain-removing components such as surface-active agents, including, but not limited to anionic surfactants such as sodium stearate, sodium palminate, sulfated butyl oleate, sodium oleate, salts of fumaric acid, glycerol, hydroxylated lecithin, sodium lauryl sulfate and chelators such as polyphosphates, which are typically employed as tartar control ingredients. In some embodiments, dental care ingredients can also include tetrasodium pyrophosphate and sodium tripolyphosphate, sodium bicarbonate, sodium acid pyrophosphate, sodium tripolyphosphate, xylitol, sodium hexametaphosphate. In some embodiments, peroxides such as carbamide peroxide, calcium peroxide, magnesium peroxide, sodium peroxide, hydrogen peroxide, and peroxydiphospate are included. In some embodiments, potassium nitrate and potassium citrate are included. Other examples can include casein glycomacropeptide, calcium casein peptone-calcium phosphate, casein phosphopeptides, casein phosphopeptide-amorphous calcium phosphate (CPP-ACP), and amorphous calcium phosphate. Still other examples can include papaine, krillase, pepsin, trypsin, lysozyme, dextranase, mutanase, glycoamylase, amylase, glucose oxidase, and combinations thereof. Further examples can include surfactants such as sodium stearate, sodium ricinoleate, and sodium lauryl sulfate surfactants for use in some embodiments to achieve increased prophylactic action and to render the dental care ingredients more cosmetically acceptable. Surfactants can preferably be detersive materials which impart to the composition detersive and foaming properties. Suitable examples of surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine. In addition to surfactants, dental care ingredients can include antibacterial agents such as, but not limited to, triclosan, chlorhexidine, zinc citrate, silver nitrate, copper, limonene, and cetyl pyridinium chloride. In some embodiments, additional anticaries agents can include fluoride ions or fluorine-providing components such as inorganic fluoride salts. In some embodiments, soluble alkali metal salts, for example, sodium fluoride, potassium fluoride, sodium fluorosilicate, ammonium fluorosilicate, sodium monofluorophosphate, as well as tin fluorides, such as stannous fluoride and stannous chloride can be included. In some embodiments, a fluorine-containing compound having a beneficial effect on the care and hygiene of the oral cavity, e.g., diminution of enamel solubility in acid and protection of the teeth against decay may also be included as an ingredient. Examples thereof include sodium fluoride, stannous fluoride, potassium fluoride, potassium stannous fluoride ($SnF_2$-KF), sodium hexafluorostannate, stannous chlorofluoride, sodium fluorozirconate, and sodium monofluorophosphate. In some embodiments, urea is included. Further examples are included in the following U.S. patents and U.S. published patent applications, the contents of all of which are incorporated in their entirety herein by reference for all purposes: U.S. Pat. Nos. 5,227,154 to Reynolds, 5,378,131 to Greenberg, 6,846,500 to Luo et al, 6,733,818 to Luo et al., 6,696,044 to Luo et al., 6,685,916 to Holme et al., 6,485,739 to Luo et al., 6,479,071 to Holme et al., 6,471,945 to Luo et al., U.S. Patent Publication Nos. 20050025721 to Holme et al., 2005008732 to Gebreselassie et al., and 20040136928 to Holme et al.

Typically, encapsulation of the active ingredient will result in a delay in the release of the predominant amount of the active ingredient during consumption of a compressible chewing gum that includes the encapsulated active ingredient (e.g., as part of a delivery system added as an ingredient to the compressible chewing gum composition). In some embodiments, the release profile of the ingredient (e.g., the dental care active ingredient) can be managed for a compressible gum by managing various characteristics of the ingredient, delivery system containing the ingredient, and/or the compressible chewing gum containing the delivery system and/or how the delivery system is made. For example, characteristics may include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the compressible chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, the release profiles of one or more flavor potentiators can be managed for a compressible gum. Flavor potentiators can consist of materials that may intensify, supplement, modify or enhance the taste and/or aroma perception of an original material without introducing a characteristic taste and/or aroma perception of their own. In some embodiments, potentiators designed to intensify, supplement, modify, or enhance the perception of flavor, sweetness, tartness, umami, kokumi, saltiness and combinations thereof can be included. In some embodiments, sweetness may be potentiated by the inclusion of monoammonium glycyrrhizinate, licorice glycyrrhizinates, citrus aurantium, maltol, ethyl maltol, vanilla, vanillin, and combinations thereof. In some embodiments, sugar acids, sodium chloride, potassium chloride, sodium acid sulfate, and combinations thereof may be included for flavor potentiation. In other examples, glutamates such as monosodium glutamate (MSG), monopotassium glutamate, hydrolyzed vegetable protein, hydrolyzed animal protein, yeast extract, and combinations thereof are included. Further examples can include glutathione, and nucleotides such as inosine monophosphate (IMP), disodium inosinate, xanthosine monophosphate, guanylate monophosphate (GMP), and combinations thereof. For bitterness blocking or taste masking, ingredients that interact with bitterness receptors to suppress bitterness or off tastes may be included. In some embodiments, adenosine monophosphate (AMP) can be included for bitterness suppression. Bitterness modification can also be accomplished by using sweetness or flavors with complementary bitter notes such as chocolate. Further examples of flavor potentiator compositions that impart kokumi are also included in U.S. Pat. No. 5,679,397 to Kuroda et al, the entire contents of which are incorporated in its entirety herein by reference.

Typically, encapsulation of a flavor potentiator will result in a delay in the release of the predominant amount of the flavor potentiator during consumption of a compressible chewing gum that includes the encapsulated flavor potentiator (e.g., as part of a delivery system added as an ingredient to the compressible chewing gum composition). In some embodiments, the release profile of the ingredient (e.g., the flavor potentiator) can be managed for a compressible gum by managing various characteristics of the ingredient, delivery system containing the ingredient, and/or the compressible chewing gum containing the delivery system and/or how the delivery system is made. For example, characteristics may include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the compressible chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, the release profiles of one or more acids may be managed for a compressible gum. Acids can include, but are not limited to acetic acid, adipic acid, ascorbic acid, butyric acid, citric acid, formic acid, fumaric acid, glyconic acid, lactic acid, phosphoric acid, malic acid, oxalic acid, succinic acid, tartaric acid and combinations thereof.

Typically, encapsulation of a food acid will result in a delay in the release of the predominant amount of the active ingredient during consumption of a compressible chewing gum that includes the encapsulated food acid (e.g., as part of a delivery system added as an ingredient to the compressible chewing gum). In some embodiments, the release profile of the ingredient (e.g., the food acid) can be managed for a compressible gum by managing various characteristics of the ingredient, delivery system containing the ingredient, and/or the compressible chewing gum containing the delivery system and/or how the delivery system is made. For example, characteristics may include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the compressible chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, the release profiles of one or more micronutrients can be managed for a compressible gum. Micronutrients can include materials that have an impact on the nutritional wellbeing of an organism even though the quantity required by the organism to have the desired effect is small relative to macronutrients such as protein, carbohydrate, and fat. Micronutrients can include, but are not limited to vitamins, minerals, enzymes, phytochemicals, antioxidants, and combinations thereof. In some embodiments, vitamins can include fat soluble vitamins such as vitamin A, vitamin D, vitamin E, and vitamin K and combinations thereof, in some embodiments, vitamins can include water soluble vitamins such as vitamin C (ascorbic acid), the B vitamins (thiamine or B1, riboflavoin or B2, niacin or B3, pyridoxine or B6, folic acid or B9, cyanocobalimin or B12, pantothenic acid, biotin), and combinations thereof.

In some embodiments, minerals can include but are not limited to sodium, magnesium, chromium, iodine, iron, manganese, calcium, copper, fluoride, potassium, phosphorous, molybdenum, selenium, zinc, and combinations thereof.

In some embodiments micronutrients can include but are not limited to L-carnitine, choline, coenzyme Q10, alpha-lipoic acid, omega-3-fatty acids, pepsin, phytase, trypsin, lipases, proteases, cellulases, and combinations thereof.

Antioxidants can include materials that scavenge free radicals. In some embodiments, antioxidants can include but are not limited to ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

In some embodiments, phytochemicals can include but are not limited to carotenoids, chlorophyll, chlorophyllin, fiber, flavanoids, anthocyanins, cyaniding, delphinidin, malvidin, pelargonidin, peonidin, petunidin, flavanols, catechin, epicatechin, epigallocatechin, epigallocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof.

Typically, encapsulation of the micronutrient will result in a delay in the release of the predominant amount of the active ingredient during consumption of a compressible chewing gum that includes the encapsulated micronutrient (e.g., as part of a delivery system added as an ingredient to the compressible chewing gum). In some embodiments, the release profile of the ingredient (e.g., the micronutrient) can be managed for a compressible gum by managing various characteristics of the ingredient, delivery system containing the ingredient, and/or the compressible chewing gum containing the delivery system and/or how the delivery system is made. For example, characteristics may include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the compressible chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, the release profiles of one or more mouth moisteners can be managed for a compressible gum. Mouth moisteners can include, but are not limited to, saliva stimulators such as acids and salts and combinations thereof. In some embodiments, acids can include acetic acid, adipic acid, ascorbic acid, butyric acid, citric acid, formic acid, fumaric acid, glyconic acid, lactic acid, phosphoric acid, malic acid, oxalic acid, succinic acid, tartaric acid and combinations thereof. Mouth moisteners can also include hydrocolloid materials that hydrate and may adhere to oral surface to provide a sensation of mouth moistening. Hydrocolloid materials can include naturally occurring materials such as plant exudates, seed gums, and seaweed extracts or they can be chemically modified materials such as cellulose, starch, or natural gum derivatives. In some embodiments, hydrocolloid materials can include pectin, gum arabic, acacia gum, alginates, agar, carageenans, guar gum, xanthan gum, locust bean gum, gelatin, gellan gum, galactomannans, tragacanth gum, karaya gum, curdlan, konjac, chitosan, xyloglucan, beta glucan, furcellaran, gum ghatti, tamarin, bacterial gums, and combinations thereof. Additionally, in some embodiments, modified natural gums such as propylene glycol alginate, carboxymethyl locust bean gum, low methoxyl pectin, and their combinations can be included. In some embodiments, modified celluloses can be included such as microcrystalline cellulose, carboxymethylcellulose (CMC), methylcellulose (MC), hydroxypropylmethylcellulose (HPMC), and hydroxypropylcellulose (MPC), and combinations thereof. Similarly, humectants which can provide a perception of mouth hydration can be included. Such humectants can include, but are not limited to glycerol, sorbitol, polyethylene glycol, erythritol, and xylitol. Additionally, in some embodiments, fats can provide a perception of mouth moistening. Such fats can include medium chain triglycerides, vegetable oils, fish oils, mineral oils, and combinations thereof. Typically, encapsulation of a mouth moistening agent will result in a delay in the release of the predominant amount of the active ingredient during consumption of a compressible chewing gum that includes the encapsulated mouth moistening agent (e.g., as part of a delivery system added as an ingredient to the compressible chewing gum). In some embodiments, the release profile of the ingredient (e.g., the mouth moistening agent) can be managed for a compressible gum by managing various characteristics of the ingredient, delivery system containing the ingredient, and/or the compressible chewing gum containing the delivery system and/or how the delivery system is made. For example, characteristics may include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the compressible chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, the release profiles of one or more ingredients that soothe the throat can be managed for a compressible gum. Throat soothing ingredients can include analgesics, anesthetics, demulcents, antiseptic, and combinations thereof. In some embodiments, analgesics/anesthetics can include menthol, phenol, hexylresorcinol, benzocaine, dyclonine hydrochloride, benzyl alcohol, salicyl alcohol, and combinations thereof. In some embodiments, demulcents can include but are not limited to slippery elm bark, pectin, gelatin, and combinations thereof. In some embodiments, antiseptic ingredients can include cetylpyridinium chloride, domiphen bromide, dequalinium chloride, and combinations thereof.

In some embodiments, antitussive ingredients such as chlophedianol hydrochloride, codeine, codeine phosphate, codeine sulfate, dextromethorphan, dextromethorphan hydrobromide, diphenhydramine citrate, and diphenhydramine hydrochloride, and combinations thereof can be included.

In some embodiments, throat soothing agents such as honey, propolis, aloe vera, glycerine, menthol and combinations thereof can be included. In still other embodiments, cough suppressants can be included. Such cough suppressants can fall into two groups: those that alter the texture or production of phlegm such as mucolytics and expectorants; and those that suppress the coughing reflex such as codeine (narcotic cough suppressants), antihistamines, dextromethorphan and isoproterenol (non-narcotic cough suppressants). In some embodiments, ingredients from either or both groups can be included.

In still other embodiments, antitussives can include, but are not limited to, the group consisting of codeine, dextromethorphan, dextrorphan, diphenhydramine, hydrocodone, noscapine, oxycodone, pentoxyverine and combinations thereof. In some embodiments, antihistamines can include, but are not limited to, acrivastine, azatadine, brompheniramine, chlo[phi]heniramine, clemastine, cyproheptadine, dexbrompheniramine, dimenhydrinate, diphenhydramine, doxylamine, hydroxyzine, meclizine, phenindamine, phenyltoloxamine, promethazine, pyrilamine, tripelennamine, triprolidine and combinations thereof. In some embodiments, non-sedating antihistamines can include, but are not limited to, astemizole, cetirizine, ebastine, fexofenadine, loratidine, terfenadine, and combinations thereof.

In some embodiments, expectorants can include, but are not limited to, ammonium chloride, guaifenesin, ipecac fluid extract, potassium iodide and combinations thereof. In some embodiments, mucolytics can include, but are not limited to, acetylcysteine, ambroxol, bromhexine and combinations thereof. In some embodiments, analgesic, antipyretic and anti-inflammatory agents can include, but are not limited to, acetaminophen, aspirin, diclofenac, diflunisal, etodolac, fenoprofen, flurbiprofen, ibuprofen, ketoprofen, ketorolac, nabumetone, naproxen, piroxicam, caffeine and mixtures thereof. In some embodiments, local anesthetics can include, but are not limited to, lidocaine, benzocaine, phenol, dyclonine, benzonotate and mixtures thereof. In some embodiments nasal decongestants and ingredients that provide the perception of nasal clearing can be included. In some embodiments, nasal decongestants can include but are not limited to phenylpropanolamine, pseudoephedrine, ephedrine, phenylephrine, oxymetazoline, and combinations thereof. In some embodiments ingredients that provide a perception of nasal clearing can include but are not limited to menthol, camphor, borneol, ephedrine, eucalyptus oil, peppermint oil, methyl salicylate, bornyl acetate, lavender oil, wasabi extracts, horseradish extracts, and combinations thereof. In some embodiments, a perception of nasal clearing can be provided by odoriferous essential oils, extracts from woods, gums, flowers and other botanicals, resins, animal secretions, and synthetic aromatic materials.

Typically, encapsulation of a throat care agent will result in a delay in the release of the predominant amount of the active ingredient during consumption of a compressible chewing gum that includes the encapsulated throat care agent (e.g. as part of a delivery system added as an ingredient to the compressible chewing gum). In some embodiments, the release profile of the ingredient (e.g. the dental care active ingredient) can be managed for a compressible gum by managing various characteristics of the ingredient, delivery system containing the ingredient, and/or the compressible chewing gum containing the delivery system and/or how the delivery system is made. For example, characteristics may include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the compressible chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, one or more colors can be included. As classified by the United States Food, Drug, and Cosmetic Act (21 C.F.R. 73), colors can include exempt from certification colors (sometimes referred to as natural even though they can be synthetically manufactured) and certified colors (sometimes referred to as artificial), or combinations thereof. In some embodiments, exempt from certification or natural colors can include, but are not limited to annatto extract, (E 160b), bixin, norbixin, astaxanthin, dehydrated beets (beet powder), beetroot red/betanin (E 162), ultramarine blue, canthaxanthin (E161g), cryptoxanthin (E161c), rubixanthin (E161d), violanxanthin (E161e), rhodoxanthin (E161f), caramel (E150(a-d)), β-apo-8'-carotenal (E160e), β-carotene (E160a), alpha carotene, gamma carotene, ethyl ester of beta-apo-8 carotenal (E160f), flavoxanthin (E161a), lutein (E161b), cochineal extract (E120); carmine (E132), carmoisine/azorubine (E122), sodium copper chlorophyllin (E141), chlorophyll (E140), toasted partially defatted cooked cottonseed flour, ferrous gluconate, ferrous lactate, grape color extract, grape skin extract (enocianina), anthocyanins (E163), haematococcus algae meal, synthetic iron oxide, iron oxides and hydroxides (E172), fruit juice, vegetable juice, dried algae meal, tagetes (Aztec marigold) meal and extract, carrot oil, corn endosperm oil, paprika, paprika oleoresin, phaffia yeast, riboflavin (E101), saffron, titanium dioxide, turmeric (E100), turmeric oleoresin, amaranth (E123), capsanthin/capsorubin (E160c), lycopene (E160d), and combinations thereof.

In some embodiments, certified colors can include, but are not limited to, FD&C blue #1, FD&C blue #2, FD&C green #3, FD&C red #3, FD&C red #40, FD&C yellow #5 and FD&C yellow #6, tartrazine (E102), quinoline yellow (E104), sunset yellow (E110), ponceau (E124), erythrosine (E127), patent blue V (E131), titanium dioxide (E171), aluminum (E173), silver (E174), gold (E175), pigment rubine/lithol rubine BK (E180), calcium carbonate (E170), carbon black (E153), black PN/brilliant black BN (E151), green S/acid brilliant green BS (E142), and combinations thereof. In some embodiments, certified colors can include FD&C aluminum lakes. These consist of the aluminum salts of FD&C dyes extended on an insoluble substrate of alumina hydrate. Additionally, in some embodiments, certified colors can be included as calcium salts. Typically, encapsulation of a color will result in a delay in the release of the predominant amount of the active ingredient during consumption of a compressible chewing gum that includes the encapsulated color (e.g., as part of a delivery system added as an ingredient to the compressible chewing gum). In some embodiments, the release profile of the ingredient (e.g., the color) can be managed by managing various characteristics of the ingredient, delivery system containing the ingredient, and/or the compressible chewing gum containing the delivery system and/or how the delivery system is made. For example, characteristics may include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the compressible chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, a delivery system or compressible chewing gum may include two or more ingredients for which managed release from the compressible chewing gum during consumption of the compressible chewing gum is desired. In some embodiments, the ingredients may be encapsulated or otherwise included separately in different delivery systems. Alternatively, in some embodiments the ingredients may be encapsulated or otherwise included in the same delivery system. As another possibility, one or more of the ingredients may be free (e.g. unencapsulated) while one or more other ingredients may be encapsulated. A compressible chewing gum may include a group of ingredients for which managed release of the group during consumption of the compressible chewing gum is desired. Groups of two or more ingredients for which managed release from a compressible chewing gum during consumption of the compressible chewing gum may be desired include, but are not limited to: color and flavor, multiple flavors, multiple colors, cooling agent and flavor, warming agent and flavor, cooling agent and warming agent, cooling agent and high-intensity sweetener, warming agent and high-intensity sweetener, multiple cooling agents (e.g., WS-3 and WS-23, WS-3 and menthyl succinate), menthol and one or more cooling agents, menthol and one or more warming agents, multiple warming agents, high-intensity sweetener(s) and tooth whitening active(s), high-intensity sweetener(s) and breath-freshening active(s), an ingredient with some bitterness and a bitterness suppressor for the ingredient, multiple high-intensity sweeteners (e.g., acesulfame-k and aspartame), multiple tooth whitening active ingredients (e.g., an abrasive ingredient and an antimicrobial ingredient), a peroxide and a nitrate, a warming agent and a polyol, a cooling agent and a polyol, multiple polyols, a warming agent and micronutrient, a cooling agent and a micronutrient, a warming agent and a mouth moistening agent, a cooling agent and a mouth moistening agent, a warming agent and a throat care agent, a cooling agent and a throat care agent, a warming agent and a food acid, a cooling agent and food acid, a warming agent and an emulsifier/surfactant, a cooling agent and an emulsifier/surfactant, a warming agent and a color, a cooling agent and a color, a warming agent and a flavor potentiator, a cooling agent and a flavor potentiator, a warming agent with sweetness potentiator, a cooling agent with a sweetness potentiator, a warming agent and an appetite suppressant, a cooling agent and an appetite suppressant, a high-intensity sweetener and a flavor, a cooling agent and a teeth-whitening agent, a warming agent and a teeth-whitening agent, a warming agent and breath-freshening agent, a cooling agent and a breath-freshening agent, a cooling agent and an effervescing system, a warming agent and an effervescing system, a warming agent and an antimicrobial agent, a cooling agent and an antimicrobial agent, multiple anticalcums ingredients, multiple remineralization ingredients, multiple surfactants, remineralization ingredients with demineralization ingredients, acidic ingredients with acid buffering ingredients, anticalculus ingredients with antibacterial ingredients, remineralization ingredients with anticalculus ingredients, anticalculus ingredients with remineralization ingredients with antibacterial ingredients, surfactant ingredients with anticalculus ingredients, surfactant ingredients with antibacterial ingredients, surfactant ingredients with remineralization ingredients, surfactants with anticalculus ingredients with antibacterial ingredients, multiple types of vitamins or minerals, multiple micronutrients, multiple acids, multiple antimicrobial ingredients, multiple breath-freshening ingredients, breath-freshening ingredients and antimicrobial ingredients, multiple appetite suppressors, acids and bases that react to effervesce, a bitter compound with a high-intensity sweetener, a cooling agent and an appetite suppressant, a warming agent and an appetite suppressant, a high-intensity sweetener and an appetite suppressant, a high-intensity sweetener with an acid, a probiotic ingredient and a prebiotic ingredient, a vitamin and a mineral, a metabolic enhancement ingredient with a macronutrient, a metabolic enhancement ingredient with a micronutrient, an enzyme with a substrate, a high-intensity sweetener with a sweetness potentiator, a cooling compound with a cooling potentiator, a flavor with a flavor potentiator, a warming compound with a warming potentiator, a flavor with salt, a high-intensity sweetener with salt, an acid with salt, a cooling compound with salt, a warming compound with salt, a flavor with a surfactant, an astringent compound with an ingredient to provide a sensation of hydration, etc. In some embodiments, the multiple ingredients may be part of the same delivery system or may be part of different delivery systems. Different delivery systems may use the same or different encapsulating materials.

Typically, encapsulation of the multiple ingredients will result in a delay in the release of the predominant amount of the multiple ingredients during consumption of a compressible chewing gum that includes the encapsulated multiple ingredients (e.g. as part of a delivery system added as an ingredient to the compressible chewing gum). This may be particularly helpful in situations wherein separate encapsulation of the ingredients may cause them to release with different release profiles. For example, different high-intensity sweeteners may have different release profiles because they have different water solubilities or differences in other characteristics. Encapsulating them together may cause them to release more simultaneously.

In some embodiments, the release profile of the multiple ingredients can be managed for a compressible gum by managing various characteristics of the multiple ingredients, the delivery system containing the multiple ingredients, and/or the compressible chewing gum containing the delivery system and/or how the delivery system is made in a manner as previously discussed above.

The active ingredients mentioned above are meant as examples of active ingredients which could be applicable in a chewing gum granule or compressed chewing gum, however, this list should not be considered as exhaustive.

Active ingredients to be applied in tablets according to embodiments of the invention may be applied as such or be included or bonded in different ways, such as being part of an inclusion complex e.g. as described in U.S. Pat. No. 5,866,179, which is hereby incorporated by reference. A resin-bonding of nicotine is described in e.g. WO 2006/000232 which is also incorporated herein by reference. Further conventional methods of applying active ingredients may obviously be applied within the scope of the invention.

The active ingredients may advantageously be applied in a gum base-containing module or a tablet-module substantially free of gum base depending on the applied type of active ingredient. If the active ingredient is of the pharmaceutical type, such ingredient may very often advantageously be comprised in a tablet module substantially free of gum base whereas taste relevant active ingredients advantageously may be added to the gum base-containing module and very often to both types of modules. The taste relevant active ingredient may both be added as separate particles which are mixed and compressed with gum base-containing particles in one module and it may be incorporated into gum base-containing granules.

In the present context, the terms granule and particle are used interchangeable in the sense that a granule or particle for use in a compression process is regarded to be a relatively small object, which together with other granules or particles may be compressed into a stable chewing gum tablet. The granules or particles may be produced in several different ways. A gum base-containing granule of particle may typically be produced substantially into the desired shape by means of an extrusion process or alternatively be produced on the basis of a gum base-containing mass which is subsequently separated into particles of a smaller size.

The following non-limiting examples illustrate different methods of obtaining a different gum base content including the evaluation of the release properties of these. The examples are meant for indicating the inventive concept; hence the mentioned examples should not be understood as exhaustive for the present invention.

EXAMPLES

Example 1

Different Gum Base Composition

An example of how to obtain different gum base content of said first and second chewing gum modules is to have different gum base compositions. Four different gum base compositions GB1-GB4 are disclosed in table 1.

TABLE 1

|  | GB1 (Wt-%) | GB2 (Wt-%) | GB3 (Wt-%) | GB4 (Wt-%) |
| --- | --- | --- | --- | --- |
| Elastomer | 10 | 10 | 15 | 15 |
| PVA | 20 | 20 | 24 | 24 |
| Natural resin | 29 | 29 | 17 | 17 |
| Filler | 9 | 17 | 13 | 13 |
| Emulsifier | 4 | 4 | 4 | 4 |
| Softener (wax and fat) | 20 | 20 | 23 | 21 |
| Antioxidant | 900 ppm | 900 ppm | 900 ppm | 900 ppm |
| Na$_2$CO$_3$ | 8 | 0 | 4 | 6 |

For a two-layer tablet with each module comprising gum base, the composition of these gum bases may be different or the same. An example would be to use GB1 as the gum base part in a first layer and use GB2 as the gum base part in a second layer. It is seen that the only active ingredient indicated in table 1 is the pH control agent Na$_2$CO$_3$. According to embodiments of the invention, this could be replaced with any other active ingredients as mentioned within this description.

Example 1 disclosed examples of content of chewing gum granules according to embodiments of the invention. Examples on how API may be added to a composition of a layer of a compressed chewing gum tablet in order to avoid possible segregation problems are shown in the following examples 2-5.

Example 2

Single Line Binding API with Flavor

The API (API: pharmaceutically active ingredient), in this example NPR, was dispersed in a mixture of grinded chewing gum granules and isomalt in a ratio of approximately 2:3.

In a next step 1.0 Wt-% peppermint flavor was sprayed into the powder mixture from a nozzle, whereby the NPR was 'glued" to both the grinded chewing gum granules and the isomalt.

In a next step the resulting mixture was sieved through an 800 μm sieve in order to remove larger cloggings.

The resulting product was a mixture of not very distinctly sized granules with NPR bound to both grinded chewing gum granules and to isomalt, whereby an improved mixing was facilitated.

Example 3

Dual Line Binding API with Flavor

The pharmaceutically active ingredient (API), in this example NPR, was dispersed with an isomalt composition.

In a next step 1.0 Wt-% peppermint flavor was sprayed into the powder mixture from a nozzle, whereby the NPR was attached to the surface of the isomalt.

Hereby particles with an approximate diameter, corresponding to the approximate diameter of the chewing gum granules to be used in the same module, were obtained, and subsequently a desired amount of chewing gum granules were added to obtain a resulting mixture.

The resulting product was a mixture of not very distinctly sized granules of which some were chewing gum granules and some were isomalt with bound NPR, whereby an improved mixing was facilitated.

Example 4

Dry Binding an API in the Pores or the Irregular Surface of a Dry Binder by Means of an Ordered Blending Process The powder blend was produced in an ordered blending process where the ingredients were blended in a specific order. The pharmaceutically active ingredient (API), in this example NPR, was mixed with a dry binder, in this example a dextrate consisting of large porous particles. The API was bound physically in the pores of the dry binder by Van der Waal forces or electrostatic forces to a degree in order for segregation to be avoided. In a next step the resulting spaces between the dry binders were filled up by isomalt.

Dry binders for use in a method like described here will typically have an average diameter of approximately 190 to 220 μm.

The resulting product was a dry bound NPR powder blend with an approximate diameter corresponding to the approximate diameter of the grinded gum base. In this mixture/composition segregation is reduced to an acceptable level due to the more equal sizes and due to the dry binder mechanism.

It should be noted, that by "more equal sizes" it is not meant that the particle sizes do actually have to be equal or almost equal, but it is meant that the difference in particle size has been significantly reduced as compared to NPR particles by themselves in blend with the chewing gum granules.

Example 5

Dry Binding an API by Means of Adhesive Contact to the Dry Binder

A dry binding process as in example 4 was repeated with the modification that small dry binder particles were now used, in this example a copovidone. Hereby the dry binding is the result of small dry binders which fill the spaces between e.g. the NPR and the further ingredients such as isomalt and mannitol. With smaller dry binders the dry binder particles are able to establish several adhesive contacts with the API and the further ingredients.

Dry binders for use in a method like described here will typically have an average diameter of approximately 65 to 75 μm.

The resulting product was a dry bound NPR powder blend with an approximate diameter corresponding to the approximate diameter of the grinded gum base.

Another method of dry binding known to the skilled person may be used within the scope of the present invention. The method is known as a Carrier Mixing in which a dry binder with an average diameter of approximately 75 to 150 μm (e.g. Mannitol EZ) is used. Here the active ingredient is binded in the internal space of the dry binder particles.

Example 6

Different Gum Base Weight

Besides as seen in example 1, a further example of how to obtain different gum base content of said first and second chewing gum modules is to have different gum base weight in each module. Table 2 discloses two different examples of two-layered chewing gum tablets, wherein the two layers in each tablet comprise a different amount of gum base by weight.

TABLE 2

| Wt-% of tablet | T1 | T2 |
|---|---|---|
| Layer 1 weight | 1000 mg | 900 mg |
| GB1 | 30.76 | 27.69 |
| Bulk sweetener | 46.16 | 41.54 |
| Layer 2 weight | 300 mg | 400 mg |
| GB1 | 9.24 | 12.31 |
| Bulk sweetener | 11.50 | 16.04 |
| NPR load 15.3 Nicotine 2.2 mg/tablet | 1.11 | 1.11 |
| Flavor | 0.231 | 0.307 |
| Tabletting aid | 1 | 1 |

In T1 layer 1 comprises an amount of gum base which is 307.6 mg, whereas layer 2 comprises an amount of gum base which is 27.72 mg.

In T2 layer 1 comprises an amount of gum base which is 249.21 mg, whereas layer 2 comprises an amount of gum base which is 49.24 mg.

Example 7

Different Gum Base Particle Sizes

A further example of how to obtain different gum base content of said first and second chewing gum modules is to have different gum base particle sizes in each module.

A composition of gum base particles will typically vary slightly in size, however to be able to obtain an improved administration of different pharmaceutically active ingredients with respect to a desired release and according to a desired synchronism through a different size of the particles, a more markedly difference in the particle sizes is needed.

Different sizes of the gum base particles may be obtained in a number of different ways, for example through grinding. An example of how to obtain different particle sizes is therefore to start from a certain composition of gum base particles and use them directly in a first layer and grind them before use in a second layer.

For example a gum base composition may consist of particles with an average diameter around 800-1500 μm and the part of the gum base particles that are being grinded may end with an average diameter of around 250-300 μm.

Table 3 discloses two different examples of two-layered chewing gum tablets, wherein the two layers in each tablet comprise a different particle size of gum base, layer 1 comprises gum base particles with an average diameter of app. 1100 μm, whereas layer 2 comprises grinded gum base particles with an average diameter of app. 280 μm.

TABLE 3

| Wt-% of tablet | T3 | T4 |
|---|---|---|
| Layer 1 weight | 650 mg | 900 mg |
| GB1 | 24.50 | 19.31 |
| Bulk sweetener | 25.50 | 49.92 |
| Layer 2 weight | 650 mg | 400 mg |
| Grinded GB1 | 24.50 | 19.31 |
| Bulk sweetener | 23.17 | 9.052 |
| NPR load 15.3 Nicotine 2.2 mg/tablet | 1.1 | 1.1 |
| Flavor | 0.231 | 0.307 |
| Tabletting aid | 1 | 1 |

Example 8

Active Ingredients in Gum Base Particles, in Composition and Combinations

A further example of how to obtain different gum base content of said first and second chewing gum modules is to have different active ingredients in each gum base in each module. Four examples of gum base compositions are shown in table 4, wherein GB6 comprises polysorbate as the active ingredient, GB7 comprises $Na_2CO_3$ as the active ingredient, GB5 comprises two active ingredients, namely both polysorbate and $Na_2CO_3$, and GB8 is an example of a gum base free of active ingredients.

The active ingredients mentioned in this example are not to be considered as limiting for which active ingredients may be used; on the contrary one or both of polysorbate and $Na_2CO_3$ in the gum bases below may be substituted with many different active ingredients to create a large number of advantageous gum bases.

It can be seen that the gum base compositions may be free of active ingredients (e.g. GB8) or comprise one (e.g. GB6 and GB7) or more (e.g. GB5) active ingredients.

TABLE 4

|  | GB5 (Wt-%) | GB6 (Wt-%) | GB7 (Wt-%) | GB8 (Wt-%) |
|---|---|---|---|---|
| Elastomer | 10 | 10 | 15 | 15 |
| PVA | 20 | 20 | 24 | 24 |
| Natural resin | 29 | 29 | 17 | 17 |
| Filler | 9 | 16.5 | 13 | 17 |
| Emulsifier | 4 | 4 | 4 | 4 |
| Softener (wax and fat) | 20 | 20 | 23 | 23 |
| Antioxidant | 900 ppm | 900 ppm | 900 ppm | 900 ppm |
| Polysorbate | 0.7 | 0.5 | 0 | 0 |
| $Na_2CO_3$ | 7.3 | 0 | 4 | 0 |

Gum bases with a various gum base content in that the content of active ingredients in the two gum bases, such as the ones shown in table 4, may be used in a two-layer tablet as indicated in table 5. Three examples of tablets (T5-T7) are shown, where the gum base content is different between the layers in that different gum bases from table 4 are used in the two layers.

In these examples the above-indicated gum bases GB7 and GB8 are the ones used; however combinations involving any of GB5, GB6, GB7 and GB8 with variations in the active ingredients as indicated above are also within the scope of the invention.

TABLE 5

| Wt-% of tablet | T5 | T6 | T7 |
|---|---|---|---|
| Layer 1 weight | 650 mg | 900 mg | 900 mg |
| GB7 | 24.50 | 19.31 | 19.31 |
| Bulk sweetener | 25.50 | 49.92 | 49.92 |
| Layer 2 weight | 650 mg | 400 mg | 400 mg |
| GB8 | 24.50 | 19.31 | 19.31 |
| Bulk sweetener | 23.17 | 9.052 | 9.915 |
| NPR load 15.3 Nicotine 2.2 mg/tablet | 1.1 | 1.1 | 0 |
| Flavor | 0.231 | 0.307 | 0.544 |
| Tabletting aid | 1 | 1 | 1 |

Advantageous combinations of active ingredients in the two layers may be:

Metformin with sodium glycolate and sodium lauryl sulfate as enhancers. A typical ratio between these may be metformin (100 parts), sodium glycolate (0.5 parts) and sodium lauryl sulfate (0.5 parts), Ceterizine (10 parts) and as enhancer Polysorbate 80 (0.5 parts), and Exenatide (Peptide API) 0.3 parts and as enhancer L-α-phosphatidylcholine Didecanoyl (DDPC) 0.3 parts.

Example 9

Combined Variations of Different Gum Base Content

The examples 1-4 have indicated various examples on how a different gum base content may be obtained through which an improved administration of different pharmaceutically active ingredients with respect to a desired release and according to a desired synchronism may be obtained.

Combinations of the above examples of obtaining different gum base content may in some embodiments be preferred.

As one example, the gum base in one of the layers of the tablets T1, T2, T5, T6 or T7 above may be replaced by a grinded gum base.

A further example could be that the gum base in one of the layers of the tablets T1-T4 above may be replaced by a gum base with a composition as disclosed in example 4.

A yet further example could be to combine all of the above, i.e. use different gum base compositions with granules of different sizes and different weights.

Example 10

Multi-Layer Tablets

Examples 1-5 have disclosed various embodiments of dual layer tablets. Also within the scope of the invention are multi-layer tablets comprising such as three, four or more layers or modules. The additional layers besides the two layers seen in the previous examples may be further layers as disclosed in the previous examples, or alternatively layers not containing gum base.

Some examples of three- and four-layered tablets are shown in table 6. The numbering of the layers does not necessarily indicate the order of the layers in the tablets.

TABLE 6

| Wt-% of tablet | T8 | T9 | T10 |
|---|---|---|---|
| Layer 1 |  |  |  |
| GB1 | 14.50 | 17.31 | 17.31 |
| Bulk sweetener | 20.50 | 26.52 | 26.52 |
| Layer 2 |  |  |  |
| Grinded GB1 | 24.00 | 19.31 | 19.31 |
| Bulk sweetener | 13.17 | 9.053 | 9.053 |
| NPR load 15.3 Nicotine 2.2 mg/tablet | 1.1 | 1.1 | 1.1 |
| Flavor | 0.230 | 0.307 | 0.307 |
| Tabletting aid | 1 | 1 | 1 |
| Layer 3 |  |  |  |
| GB1 | 0 | 5.00 | 0 |
| Bulk sweetener | 25.50 | 20.40 | 10.20 |
| Layer 4 |  |  |  |
| GB1 | 0 | 0 | 5.00 |
| Bulk sweetener | 0 | 0 | 10.20 |

Example 11

Release Control—Different Composition

Control of the release was tested for chewing gum tablets comprising two modules with different gum base content and a different active ingredient in each of them.

In this example a gum base content different with respect to composition was investigated. In the first layer the active ingredient (NPR) was added to the chewing gum composition outside the gum base granules and in the second layer the active ingredient ($Na_2CO_3$ pH control agent) was added approximately 50 Wt-% to the chewing gum composition outside the gum base granules and approximately 50 Wt-% incorporated in the granules. A fast release of part of the pH control agent was seen which quickly ensured a desired pH in the mouth cavity, whereby the following slower release of NPR was given good conditions in that the pH was initially set to a value where the NPR was maintained essentially on non-ionic form and the slower release of the remaining part of the pH control agent (contained inside the granules) of the second layer helped to maintain this desired pH in the mouth cavity.

To ensure that the result of this example was not due to different API in the two layers, the example was further supplemented with a test with the same amount of a same API incorporated in the granules and added directly to the composition respectively, where it was again seen that the release was dependent on the chewing gum composition The conclusion of this example was that a desired release or a desired synchronism could be obtained from different compositions of the gum bases and improved control of release profiles was made possible.

Example 12

Release Control—Different Weight

Control of the release was tested for chewing gum tablets comprising two modules with different gum base content and a different active ingredient in each of them.

In this example a gum base content different with respect to weight was investigated. In the first layer the active ingredient (NPR) was present with a large amount of gum base and in the second layer the active ingredient ($Na_2CO_3$ pH control agent) was present with a small amount of gum base. The release of the pH control agent was seen to occur faster than the release of the NPR, whereby a desired pH in the mouth cavity was obtained relatively fast, and the release of NPR was given good conditions in that the pH relatively quickly reached a value where the NPR was maintained essentially on non-ionic form.

To ensure that the result of this example was not due to different API in the two layers, the example was further supplemented with a test with two different weights of the same API in the compositions in the two layers, where it was again seen that the release was dependent on the weight of the gum base content in the chewing gum composition.

The conclusion of this example was that a desired release or a desired synchronism could be obtained from different weights of the gum bases and improved control of release profiles was made possible. Hence it seems that release profile control may be controlled by selecting a certain amount of gum base for each module.

Example 13

Release Control—Different Size of Applied Chewing Gum Granules

Control of the release was tested for chewing gum tablets comprising two modules with different gum base content and a different active ingredient in each of them.

In this example a gum base content different with respect to size of applied chewing gum granules was investigated.

In the first layer the active ingredient (NPR) was present with chewing gum granules with a relatively smaller average diameter and in the second layer the active ingredient ($Na_2CO_3$ pH control agent) was present with chewing gum granules with a relatively larger average diameter. The release of pH control agent was seen to occur faster than the release of the NPR, whereby a desired pH in the mouth cavity was obtained relatively fast.

To ensure that the result of this example was not due to different API in the two layers, the example was further supplemented with a test with the same API in two compositions of different chewing gum granule sizes. Here it was again seen that the release was dependent on the size of the chewing gum granules used in the layers of the gum base content in the chewing gum composition.

The conclusion of this example was that a desired release or a desired synchronism could be obtained from different size of the applied chewing gum granules and control of release profiles was made possible.

What is claimed is:

1. A compressed chewing gum tablet comprising at least a first and a second chewing gum module,
    said first chewing gum module comprising a first chewing gum composition comprising at least a first active ingredient and chewing gum granules containing gum base,
    said second chewing gum module comprising a second chewing gum composition comprising at least a second active ingredient and chewing gum granules containing gum base,
    wherein the first chewing gum composition is different in composition than the second chewing gum composition,
    wherein said first active ingredient is nicotine and said second active ingredient is a pH control agent; and
    wherein at least part of the pH control agent is contained within the second chewing gum module outside the chewing gum granules of the second chewing gum module, and wherein nicotine is contained within said chewing gum granules of the first chewing gum module.

2. The compressed chewing gum tablet according to claim 1, wherein said first chewing gum composition comprises a further active ingredient different from said first active ingredient.

3. The compressed chewing gum tablet according to claim 1, wherein said second chewing gum composition comprises a further active ingredient different from said second active ingredient.

4. The compressed chewing gum tablet according to claim 1, wherein said active ingredients in said first chewing gum module are at least partly contained within said chewing gum granules.

5. The compressed chewing gum tablet according to claim 1, wherein said active ingredients in said second chewing gum module are at least partly contained within said chewing gum granules.

6. The compressed chewing gum tablet according to claim 1, wherein the gum base content of said first and secondary gum modules is different with respect to at least one of composition, weight, size of applied chewing gum granules, and degree of mixing with the active ingredient.

7. The compressed chewing gum tablet according to claim 1, wherein at least one of said first and second chewing gum composition facilitates a bi-phasic release of said second active ingredient.

8. The compressed chewing gum tablet according to claim 1, wherein said compressed chewing gum tablet comprises at least three individual coherent compressed modules.

9. The compressed chewing gum tablet according to claim 1, wherein the chewing gum granules have been granulated to an average particle size of below 1500 μm and further grinded to an average particle size of below 800 μm.

10. The compressed chewing gum tablet according to claim 1, wherein said chewing gum granules of the first chewing gum module comprise at least a part of said nicotine.

* * * * *